US012792016B2

(12) United States Patent
Grimm et al.

(10) Patent No.: US 12,792,016 B2
(45) Date of Patent: Nov. 10, 2026

(54) CONTROLLING AND MONITORING A PROCESS TO PRODUCE A CHEMICAL, PHARMACEUTICAL OR BIOTECHNOLOGICAL PRODUCT

(71) Applicant: Sartorius Stedim Biotech GmbH, Göttingen (DE)

(72) Inventors: Christian Grimm, Göttingen (DE); Mario Becker, Göttingen (DE); Lars Böttcher, Göttingen (DE); Thorsten Adams, Göttingen (DE)

(73) Assignee: Sartorius Stedim Biotech GmbH (DE)

(*) Notice: Subject to any disclaimer, the term of this patent is extended or adjusted under 35 U.S.C. 154(b) by 1606 days.

(21) Appl. No.: 16/329,183

(22) PCT Filed: May 11, 2017

(86) PCT No.: PCT/EP2017/061303
§ 371 (c)(1),
(2) Date: Feb. 27, 2019

(87) PCT Pub. No.: WO2018/041423
PCT Pub. Date: Mar. 8, 2018

(65) Prior Publication Data
US 2019/0219992 A1 Jul. 18, 2019

(30) Foreign Application Priority Data
Aug. 31, 2016 (EP) .................................... 16001899

(51) Int. Cl.
*G05B 19/418* (2006.01)
*C12M 1/34* (2006.01)

(52) U.S. Cl.
CPC ....... *G05B 19/41835* (2013.01); *C12M 41/36* (2013.01); *G05B 19/4181* (2013.01);
(Continued)

(58) Field of Classification Search
None
See application file for complete search history.

(56) References Cited

U.S. PATENT DOCUMENTS

2008/0127186 A1 5/2008 Kanodia et al.
2008/0133044 A1 6/2008 Grieb et al.
(Continued)

FOREIGN PATENT DOCUMENTS

JP 2007 011686 A 1/2007

OTHER PUBLICATIONS

Largoni, M., Facco, P., Bernini, D., Bezzo, F. and Barolo, M., 2015. Quality-by-Design approach to monitor the operation of a batch bioreactor in an industrial avian vaccine manufacturing process. Journal of biotechnology, 211, pp. 87-96. (Year: 2015).*
(Continued)

*Primary Examiner* — G. Steven Vanni
*Assistant Examiner* — Meredith Abbott Vassell
(74) *Attorney, Agent, or Firm* — Klarquist Sparkman, LLP

(57) ABSTRACT

A computer system and computer-implemented method are described for controlling and monitoring a process to produce a chemical, pharmaceutical or biotechnological product. The method includes providing a database that stores sets of process parameters to control and monitor a plurality of processes performed in order to produce products, receiving a set of characterizing process parameters that characterize the process, identifying a first set process parameters from the stored sets of process parameters, and controlling and monitoring the process using a successful trajectory that includes a time-based profile of measurements.

14 Claims, 18 Drawing Sheets

(52) U.S. Cl.
CPC ... *G05B 19/4185* (2013.01); *G05B 19/41865* (2013.01); *G05B 19/41875* (2013.01); *G05B 2219/31265* (2013.01); *G05B 2219/32191* (2013.01); *G05B 2219/32201* (2013.01); *G05B 2219/42001* (2013.01); *Y02P 90/02* (2015.11)

(56) References Cited

U.S. PATENT DOCUMENTS

| | | | |
|---|---|---|---|
| 2009/0143873 | A1 | 6/2009 | Navratil et al. |
| 2011/0288660 | A1 | 11/2011 | Wojsznis et al. |
| 2012/0003623 | A1* | 1/2012 | Bartee .......... G05B 2219/31265 702/19 |

OTHER PUBLICATIONS

Kakes, E., 2008. SCADA Systems for Bioreactors. Practical Fermentation Technology, pp. 289-322. (Year: 2008).*

Sandor, M., Rüdinger, F., Solle, D., Bienert, R., Grimm, C., Groß, S. and Scheper, T., 2013, December. NIR-spectroscopy for bioprocess monitoring & control. In BMC proceedings (vol. 7, pp. 1-3). BioMed Central. (Year: 2013).*

Simutis, R. and Lübbert, A., 2015. Bioreactor control improves bioprocess performance. Biotechnology journal, 10(8), pp. 1115-1130. (Year: 2015).*

Li, W., Han, H., Cheng, Z., Zhang, Y., Liu, S. and Qu, H., Mar. 2016. A feasibility research on the monitoring of traditional Chinese medicine production process using NIR-based multivariate process trajectories. Sensors and Actuators B: Chemical, 231, pp. 313-323. (Year: 2016).*

Lopez-Montero, E.B., Wan, J. and Marjanovic, O., 2015. Trajectory tracking of batch product quality using intermittent measurements and moving window estimation. Journal of Process Control, 25, pp. 115-128. (Year: 2015).*

Sandor, M., Rüdinger, F., Solle, D., Bienert, R., Grimm, C. and Scheper, T., 2013. NIR spectroscopy for process monitoring and control in mammalian cell cultivation. BioProcess Int, 11(8), 7 pages). (Year: 2013).*

McClure, Robert W, "Statistically Derived Static Process Models." In *1986 American Control Conference,* pp. 1182-1186. IEEE, 1986.

International Search Report and Written Opinion, mailed Jun. 19, 2017, of PCT Patent Application No. PCT/EP2017/061303, 17 pages.

MacGregor et al., "Statistical process control of multivariate processes," *Control Engineering Practice* 3(3): 403-414, 1995.

Nomikos et al., "Monitoring batch processes using multiway principal component analysis," *AIChE Journal* 40(8): 1361-1375, 1994.

* cited by examiner

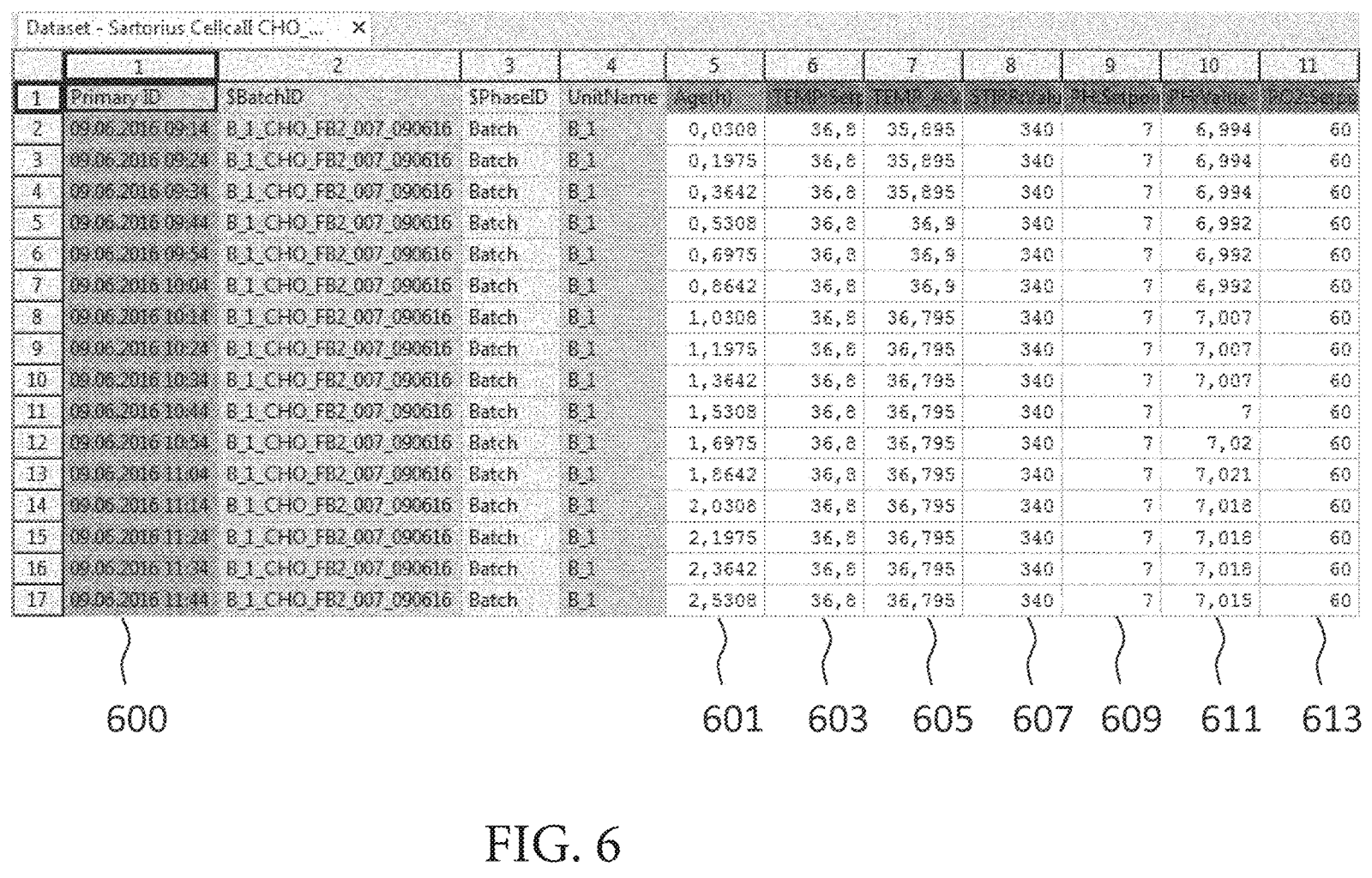

Dataset - Sartorius Cellcall CHO_...

| | 1 | 2 | 3 | 4 | 5 | 6 | 7 | 8 | 9 | 10 | 11 |
|---|---|---|---|---|---|---|---|---|---|---|---|
| 1 | Primary ID | $BatchID | $PhaseID | UnitName | [illegible] | [illegible] | [illegible] | [illegible] | [illegible] | [illegible] | [illegible] |
| 2 | 09.06.2016 09:14 | B_1_CHO_FB2_007_090616 | Batch | B_1 | 0,0308 | 36,8 | 35,895 | 340 | 7 | 6,994 | 60 |
| 3 | 09.06.2016 09:24 | B_1_CHO_FB2_007_090616 | Batch | B_1 | 0,1975 | 36,8 | 35,895 | 340 | 7 | 6,994 | 60 |
| 4 | 09.06.2016 09:34 | B_1_CHO_FB2_007_090616 | Batch | B_1 | 0,3642 | 36,8 | 35,895 | 340 | 7 | 6,994 | 60 |
| 5 | 09.06.2016 09:44 | B_1_CHO_FB2_007_090616 | Batch | B_1 | 0,5308 | 36,8 | 36,9 | 340 | 7 | 6,992 | 60 |
| 6 | 09.06.2016 09:54 | B_1_CHO_FB2_007_090616 | Batch | B_1 | 0,6975 | 36,8 | 36,9 | 340 | 7 | 6,992 | 60 |
| 7 | 09.06.2016 10:04 | B_1_CHO_FB2_007_090616 | Batch | B_1 | 0,8642 | 36,8 | 36,9 | 340 | 7 | 6,992 | 60 |
| 8 | 09.06.2016 10:14 | B_1_CHO_FB2_007_090616 | Batch | B_1 | 1,0308 | 36,8 | 36,795 | 340 | 7 | 7,007 | 60 |
| 9 | 09.06.2016 10:24 | B_1_CHO_FB2_007_090616 | Batch | B_1 | 1,1975 | 36,8 | 36,795 | 340 | 7 | 7,007 | 60 |
| 10 | 09.06.2016 10:34 | B_1_CHO_FB2_007_090616 | Batch | B_1 | 1,3642 | 36,8 | 36,795 | 340 | 7 | 7,007 | 60 |
| 11 | 09.06.2016 10:44 | B_1_CHO_FB2_007_090616 | Batch | B_1 | 1,5308 | 36,8 | 36,795 | 340 | 7 | 7 | 60 |
| 12 | 09.06.2016 10:54 | B_1_CHO_FB2_007_090616 | Batch | B_1 | 1,6975 | 36,8 | 36,795 | 340 | 7 | 7,02 | 60 |
| 13 | 09.06.2016 11:04 | B_1_CHO_FB2_007_090616 | Batch | B_1 | 1,8642 | 36,8 | 36,795 | 340 | 7 | 7,021 | 60 |
| 14 | 09.06.2016 11:14 | B_1_CHO_FB2_007_090616 | Batch | B_1 | 2,0308 | 36,8 | 36,795 | 340 | 7 | 7,018 | 60 |
| 15 | 09.06.2016 11:24 | B_1_CHO_FB2_007_090616 | Batch | B_1 | 2,1975 | 36,8 | 36,795 | 340 | 7 | 7,018 | 60 |
| 16 | 09.06.2016 11:34 | B_1_CHO_FB2_007_090616 | Batch | B_1 | 2,3642 | 36,8 | 36,795 | 340 | 7 | 7,018 | 60 |
| 17 | 09.06.2016 11:44 | B_1_CHO_FB2_007_090616 | Batch | B_1 | 2,5308 | 36,8 | 36,795 | 340 | 7 | 7,015 | 60 |

600 601 603 605 607 609 611 613

FIG. 6

CONTROLLING AND MONITORING A PROCESS TO PRODUCE A CHEMICAL, PHARMACEUTICAL OR BIOTECHNOLOGICAL PRODUCT

CROSS REFERENCE TO RELATED APPLICATIONS

This is the U.S. National Stage of International Application No. PCT/EP2017/061303, filed May 11, 2017, which in turn claims the benefit of European Patent Application No. 16 001 899.0 filed Aug. 31, 2016. European Patent Application No. 16 001 899.0 is incorporated herein by reference in its entirety.

The technical field of the present application is processes for the production of chemical, pharmaceutical, or biotechnological products. In particular, aspects of the application relate to controlling and monitoring an industrial process characterized by multivariate behavior. Each variable or parameter characterizing the process specifies how the process will be performed or executed and has an effect on the product that is ultimately produced via the process.

Examples of processes according to the present application are industrial processes, particularly biopharmaceutical processes. A process of the present application may involve chemical or microbiological conversion of material in conjunction with the transfer of mass, heat, and energy. The process may be scale dependent; in other words, the process may behave differently on a small scale (e.g., in a laboratory) in comparison to a large scale (e.g., in production). The process may include heterogeneous chemical reactions. The process may be a batch process, which is an example of an industrial, biopharmaceutical process. The batch process may involve producing small amounts of a product, and gradually scaling up to larger amounts. The batch process may involve chemical or biological reactions that take time to complete.

In batch processing, multiple batches may be produced, possibly at different scales (e.g. five liters, ten liters, one hundred liters). There may be a pause between each batch, e.g. to set up a new batch.

The process of the present application may be a continuous process, designed such that growth is limited by the availability of one or two (or more) limiting components of a medium. When an initial quantity of one of the limiting components is exhausted, growth ceases if a steady stage is reached, but growth may be renewed by the addition of the limiting component(s). Addition of nutrients may increase the volume of a medium in a vessel in which the product is produced. Volume of the medium may drain off as an overflow, which can be collected and used for recovery of the product.

The process of the present application may be a fed batch process. Accordingly, the process may be carried out in a fermentor designed to accommodate increasing volumes. The production system of the fed batch process may always be at a quasi-steady state. One or more nutrients may be fed into the fermentor during cultivation and the product may remain in the medium until the end of the run. The fed batch process may involve a culture in which a base medium supports initial cell culture and a feed medium is added to prevent nutrient depletion. The base medium and the feed medium may be considered parts of the medium in the vessel.

There are various challenges involved in industrial production of products. In particular, production of a multitude of different products on the same equipment complicates control of the process. A wide range of operating conditions and changes in the process create measurement and control challenges. Added challenges in assembling, cleaning, and sequencing of the process data for analysis may arise. Each process parameter (e.g. input or control set point) can potentially impact some or all measurements recorded during the process. Further, it may take some time for changes to inputs or to conditions of the process to have an effect, which may make it challenging to determine whether the process is proceeding as it should. The time needed to complete the process may vary, e.g. in view of pauses or restarts to add ingredients or wait for equipment availability.

Many measurements taken from the process may be collinear, i.e. related to each other and responding to process input changes in the same manner. Accordingly, it may be possible to infer values of many process measurements from a limited number of process measurements.

Aspects of the present application may be particularly useful for a user or organization that has determined a product to be produced and some or all of the quality attributes of the product, but does not know an approach that can be used to successfully produce the product or what measurements to expect when carrying out a process to produce the product.

Techniques described in the present application may be particularly helpful for small to medium sized organizations that carry out processes to make about 15 milliliters to about 2000 liters of a product. In addition, techniques described in the present application may be useful for scaling up. For example, an organization may start with ingredients to produce five liters of a product and then gradually scale up to produce 250 liters of the product. Multiple batches may be produced between a five liter batch and a 250 liter batch.

Further, the ingredients to produce a batch may be expensive. Accordingly, it may be desirable to ensure that as many batches as possible are successful so that expensive ingredients are not wasted. For example, ingredients to produce a 200 liter batch of a biopharmaceutical product may cost up to € 100.000 (one hundred thousand Euros).

Examples of inputs or ingredients for a process according to the present application may include biomass, such as bacteria, yeasts, molds, animal cells, plant cells. Further ingredients may include chemical compounds, proteins, such as enzymes, various substrates.

Possible products may include a transformed substrate, baker's yeast, lactic acid culture, lipase, invertase, rennet.

Further exemplary biopharmaceutical products that can be produced according to the techniques described in the present application include the following; recombinant and non-recombinant proteins, vaccines, gene vectors, DNA, RNA, antibiotics, secondary metabolites, growth factors, cells for cell therapy or regenerative medicine, half-synthesized products (e.g. artificial organs). Various production systems may be used to facilitate the process, e.g. cell based systems such as animal cells (e.g. CHO, HEK, PerC6, VERO, MDCK), insect cells (e.g. SF9, SF21), microorganisms (e.g. *E. coli, S. cerevisiae, P. pastoris*, etc.), algae, plant cells, cell free expression systems (cell extracts, recombinant ribosomal systems, etc.), primary cells, stem cells, native and gene manipulated patient specific cells, matrix based cell systems.

Techniques described in the present application may be useful for bioreactor processes, and for processes carried out at other levels of production. The process may include (i.e. may be performed according to) at least two process parameters that have an influence on performance of the process (e.g., product titer, quality attributes) and the product produced by the process.

According to an aspect, a computer implemented method of controlling and monitoring a process to produce a chemical, pharmaceutical, or biotechnological product is provided. The process may be an industrial process, such as a biopharmaceutical process. The product may be a biological or biopharmaceutical product. Controlling and monitoring the process may include performing the process and attempting to insure that the process results in a product that meets specified attributes (e.g. quality attributes).

A quality attribute may be a physical, chemical, biological or microbiological property that should be within an appropriate limit, range, or distribution to ensure desired product quality.

Critical quality attributes may be a proper subset of the quality attributes determined to be particularly relevant for assessing the quality of the product. Alternatively, the critical quality attributes may include all the quality attributes.

The method comprises providing a database. The database may be connected to a network, such that the database is accessible by multiple users. In particular, the database may be accessible by users from a variety of organizations with no connection to each other. Each of the users may be able to store and retrieve data from the database. The database may be implemented as a cloud database, i.e. a database that runs on a cloud computing platform. In other words, the database may be accessible over the Internet via a provider that makes shared processing resources and data available to computers and other devices on demand. The database may be implemented using a virtual machine image or a database service. The database may use an SQL based or NoSQL data model.

The database stores sets of process parameters to control and monitor respective ones of a plurality of processes performed in order to produce products. The database may provide access control such that some of the process parameters are public and accessible by all users of the database and some process parameters are private and only accessible by a limited number of users or one particular user. Each of the products produced by the plurality of processes may meet specified quality attributes (i.e. attributes defining a standard or specification for the product).

Each of the stored sets of process parameters is associated with a successful trajectory of a respective one of the processes performed according to the respective set of process parameters. The database may be relational and the association may be implemented via a relation in the database. The association could also be implemented using a link, a pointer, or other means of connecting elements. Each successful trajectory is a time based profile of measurements recording during performance of the respective process.

Each trajectory may be understood to summarize and provide an overview of associated process data. Each trajectory may be implemented as a curve or graph that describes an associated process. The trajectory may also be referred to as a control chart (or a batch control chart in the context of an associated batch process). In the context of a batch process, each batch may have its own corresponding trajectory. A successful trajectory for the respective process may be derived from all of the batch trajectories. More specifically, the successful trajectory may be an average of all the batch trajectories that resulted in products meeting the quality attributes.

The method further comprises receiving a set of characterizing process parameters that characterize the process. Each of the characterizing process parameters may describe the process or determine how the process is performed. For example, some of the characterizing process parameters may be derived via multivariate analysis (e.g. multivariate statistical techniques). The characterizing process parameters may include control set points that control how the process is performed. Examples of control set points are process duration, temperature, stirring/agitating speed, acidity/basicity, dissolved oxygen level.

The method further comprises identifying a first set of process parameters from the stored sets of process parameters, the first set of process parameters having a specified degree of similarity to the set of characterizing process parameters. The first set of process parameters is associated with a first successful trajectory. The first successful trajectory is one of the successful trajectories. The specified degree of similarity may be predetermined such that the first set of process parameters is the first one of the stored sets of process parameters to be found having the specified degree of similarity (e.g. 80% similarity) to the set of characterizing process parameters. Alternatively, the first set of process parameters may be one of the stored sets of process parameters having the greatest degree of similarity to the set of characterizing process parameters according to similarity comparisons of all stored sets of process parameters to the characterizing process parameters. The specified degree of similarity may be specified via a variable or an external function. The degree of similarity between the stored sets of process parameters and the characterizing process parameters may be determined by comparing a numerical description of the process being controlled and monitored with the numerical descriptions of the respective processes performed according to the stored sets of process parameters. Numerical descriptions of processes are discussed in more detail below.

The method further comprises controlling and monitoring the process using the first successful trajectory. In some cases, the first set of process parameters may include additional process parameters and/or parameter values that are not included in the characterizing process parameters. In such cases, the controlling and monitoring of the process may be carried out using the first successful trajectory and the first set of process parameters/values.

The controlling and monitoring of the process comprises recording measurements of the process. Measurements may be performed inline, online, atline, or offline. Inline measurements may be obtained using probes, sensors, or measuring devices placed in the product to be produced. Examples of inline measurements are pH, temperature, pressure, density. The measurements may be carried out at specified intervals throughout the process and may correspond to process parameters that have a defined confidence interval. Inline measurements generally do not require removal of a sample of the product.

Offline measurements may require a sample of the product to be diverted for in-depth analysis. In some cases offline measurements may be performed once for a batch. Examples of offline measurements are a product titer and a glycosylation pattern. Online and atline measurements may also involve removal or diversion of a sample of the product to be produced. Online and atline measurements may involve less analysis than offline measurements. Online measurements may be more fully automated than atline measurements and may be performed closer to where the process is being performed. Atline measurements may require more time than online measurements and more manual intervention than online measurements. However, atline measurements might not involve the time, the level of analysis and manual intervention required for offline measurements.

Controlling and monitoring the process using the first successful trajectory further comprises estimating a trajectory of the process based on the recorded measurements. The estimation may be performed using inline, online, atline, and offline measurements or some combination of the four. The estimation of the trajectory may be performed using multivariate analysis.

In some cases, the process can be controlled and monitored until a finishing condition is met using the first successful trajectory. Once the finishing condition is met, a determination may be made that the process is complete. In other cases, further steps may be carried out, as discussed in the following.

Controlling and monitoring the process using the first successful trajectory may further comprise comparing the estimated trajectory with the first successful trajectory. The comparison may be carried out by comparing a point on the estimated trajectory with a corresponding point on the first successful trajectory. In some cases, each trajectory represents numerical descriptions of process measurements over time (i.e. each point on the trajectory is a numerical description of process measurements at a particular time). Accordingly, at a particular point in time after the start of the process (e.g. 20 seconds) a numerical description of measurements of the process can be derived from the recorded measurements of the process. Derived numerical descriptions of the recorded measurements can be used, possibly in conjunction with the characterizing process parameters, to estimate the entire trajectory (or some part of the future trajectory) of the process. The trajectory of the process may be estimated using multivariate statistical techniques (e.g. principal component analysis, as described in more detail below). The estimated trajectory can be compared to the first successful trajectory (or the corresponding part of the first successful trajectory).

Controlling and monitoring the process using the first successful trajectory may further comprise, when a difference between the estimated trajectory and the first successful trajectory fails a confidence criterion, comparing the recorded measurements and the set of characterizing process parameters to a plurality of the stored sets of process parameters. The comparing may involve comparing the combination of the recorded measurement and the set characterizing process parameters with the plurality of stored sets of process parameters. The comparison may be carried out by deriving a numerical description of the process from the recorded measurements and the set of characterizing process parameters and comparing the derived numerical description to numerical descriptions corresponding to each of the plurality of the stored sets of process parameters.

The method further may comprise determining, based on the comparison, whether a second set of process parameters from the plurality of stored sets of process parameters has a greater degree of similarity to the set of characterizing process parameters and the recorded measurements than the first set of process parameters. When the second set of process parameters is determined, the method may further comprise controlling and monitoring the process using a second successful trajectory associated with the second set of process parameters. The second successful trajectory may be one of the successful trajectories associated with the stored sets of process parameters. Once the process is being controlled and monitored using the second successful trajectory, it is possible that the first successful trajectory will no longer be used.

The comparing of the estimated trajectory with the first successful trajectory (or the successful trajectory currently being used to control and monitor the process) may be performed periodically. When a difference between the first (or current) successful trajectory fails the confidence criterion, the steps discussed above with respect to determining the second set of process parameters may be carried out in order to determine a further set of process parameters and a further trajectory associated with the further set of process parameters for use in continuing to control and monitor the process.

The method may further comprise continuing to perform the process until a finishing condition is met. When the finishing condition is met, the method may further comprise determining that the process is complete.

Identifying the first set of process parameters may comprise identifying sets of candidate process parameters from the stored sets of process parameters and identifying the first set of process parameters from the sets of candidate process parameters. The sets of candidate process parameters may be identified based on user input, or text analysis of text values of the characterizing process parameters. Text values of the characterizing process parameters may also be referred to as process metadata, which may include cell strain, product name, batch type. The received input may be provided via a predefined selection box, such as a list box, that can be used to specify general characteristics of the process.

The candidate process parameters may include the plurality of the stored sets of process parameters compared with the recorded measurements and the set of characterizing process parameters.

The characterizing process parameters and the stored sets of process parameters may include one or more of the following: numerical values, text values, Boolean values.

Identifying the first set of stored process parameters may comprise comparing, via multivariate data analysis, numerical values of the set of characterizing process parameters with numerical values of the sets of stored process parameters. The multivariate analysis may also involve a comparison of text values, e.g. cell type.

The comparison may involve deriving a numerical description of the process based on the characterizing process parameters and comparing the derived numerical description with numerical descriptions derived from numerical values of the sets of stored process parameters.

As an alternative to the comparison of the numerical descriptions of the processes described above, identifying the first set of process parameters comprises comparing the characterizing control set point with respective control set points of the sets of stored process parameters. The comparison may involve multivariate data analysis. For example, if the characterizing control set point indicates that the process should be performed at a certain temperature, this temperature set point could be compared with temperature set points of the sets of stored process parameters in order to identify the first set of process parameters from the stored sets of process parameters. Other set point comparisons could also be performed in order to identify the first set of process parameters.

The numerical values of the set of characterizing process parameters may include a characterizing control set point, and/or a characterizing confidence interval. The numerical values of the first set of stored process parameters may include a first control set point. The numerical values of the first set of stored process parameters may include a first confidence interval. The numerical values of the second set of stored process parameters may include at least one of the following: a second control set point, a second confidence interval. The numerical values of each of the sets of stored process parameters may include at least one of the following: a respective control set point, a respective confidence interval.

Each of the successful trajectories associated with respective processes performed according to the stored sets of process parameters may be calculated as a mean of multiple trajectories derived from performing the same process. Each of the multiple trajectories may be derived from a different batch of the process. Accordingly, each process in the database may be associated with multiple batches. Each batch may have its own trajectory. The successful trajectory for the process may be the mean of the trajectories associated with each batch of the process. Trajectories associated with unsuccessful batches, i.e. batches that do not meet specified quality attributes, may be excluded from batch trajectories used to derive a successful trajectory.

Identifying the first set of process parameters may comprise performing a similarity comparison between the characterizing process parameters and a plurality of the stored sets of process parameters, e.g. using multivariate statistical techniques such as principal component analysis. Principal component analysis may be implemented as follows.

Determining an initial principal component from a plurality of the characterizing process parameters. Identifying the first set of process parameters may further comprise determining an initial numerical description of the process as a function of the initial principle component. Identifying the first set of process parameters may further comprise comparing the initial numerical description of the process to numerical descriptions of processes included in the stored sets of process parameters. In order to establish the specified degree of similarity, a numerical description of a respective process performed according to the first set of stored process parameters may be closer to the initial numerical description of the process than at least one other numerical description of a respective one of the plurality of processes.

Identifying the first set of process parameters may comprise determining, via multivariate analysis, stored process parameters that have an effect on quality attributes included in the characterizing process parameters. The determining may comprise ranking parameters of the stored process parameters from those having the most significant effect on the included quality attributes to those having the least significant effect on the included quality attributes. In some cases, the determined process parameters are not included in the characterizing process parameters. In addition or alternatively, the determined process parameters may have associated values that are not included in the characterizing process parameters. Further, the first set of stored process parameters may include the determined process parameters. In addition, the determined process parameters included in the first set of stored process parameters may have a relatively significant effect on the included quality attributes according to the ranking.

Any of the sets of process parameters described above may include quality attributes. Quality attributes may be chemical, physical, biological or microbiological characteristics that can be defined and measured to ensure final product outputs are within acceptable limits. Quality attributes may include one or more of the following: misincorporations, glycosylation, recovery, protein misfolds, aggregation, product concentration, protein concentration, moisture, foreign particles, total mass, drug release rate, total drug content, product titer, power consumption while carrying out the process. Misincorporations, recovery, misfolds and aggregation may be determined via high performance liquid chromatography.

Identifying the second set of process parameters may comprise performing a similarity comparison, similar to the similarity comparison described above. In particular the similarity comparison may include the application of multivariate statistical techniques, such as principal component analysis. Principal component analysis may be implemented as follows.

Determining a principal component that describes at least one of the recorded measurements corresponding to one of the characterizing process parameters. For example, if the characterizing process parameter is temperature, the recorded measurement may be the measurement of the temperature of the product being produced at a particular time, e.g. 30° C. at time t, where time t may be measured in seconds from the start of the process. A first principal component may be derived from the first set of process parameters and a second principal component may be derived from the second set of process parameters. Each of the principal components may describe a recorded measurement corresponding to the characterizing process parameter. In particular, continuing the example, the first principal component may describe a temperature recorded during performance of the process performed according to the first set of process parameters. Each of the principal components may describe multiple recorded measurements corresponding to the characterizing process parameter. Further, each of the principal components may describe multiple recorded measures for a plurality of the characterizing process parameters. In some cases, each of the principal components may describe all recorded measurements corresponding to the characterizing process parameter that were recorded during performance of the respective process. Further each of the principal components may describe all recorded measurements corresponding to multiple characterizing process parameters. The second set of process parameters may be identified based on a comparison of values calculated from the principal components.

Determining the second set of process parameters may comprise determining a plurality of principal components from the characterizing process parameters and the recorded measurements. Accordingly, a characterizing numerical description of the process may be calculated as a function of the plurality of principal components. A first numerical description of the respective process performed according to the first set of process parameters may be calculated as a function of a plurality of principal components derived from the first set of process parameters. As second numerical description of the respective process performed according to the second set of process parameters may be calculated as a function of a plurality of principal components derived from the second set of process parameters.

It may be that each of the principle components is a linear combination of process parameters. Principal component analysis is described in more detail in "Statistical process control of multivariate processes", J. F. MacGregor and T. Kurt', 1995 and in "Multi- and Megavariate Data Analysis: Basic Principles and Applications", L. Ericson, et al., 3rd revised edition, 2013. Other suitable multivariate statistical techniques (e.g. partial least squares) may also be used.

Determining the second set of process parameters may comprise determining that the characterizing numerical description is closer to the second numerical description than the first numerical description. Determining that the characterizing numerical description is closer to the second numerical description than the first numerical description may be carried out via a similarity measure. Examples of similarity measures include Euclidean distance, Hotellings T2 range, distance to model (DModX), and Mahalanobis distance.

For example, each numerical description may be represented by Cartesian coordinates. Accordingly, it may be found that the Euclidean distance between the characterizing numerical description and the second numerical description is less than the Euclidean distance between the characterizing numerical description and the first numerical description. Hotellings T2 range may be understood as a measure of how far an observation is from the center. Accordingly, the characterizing numerical description may be understood as the center and numerical descriptions of the stored sets of process parameters may be understood as observations. Distance to model (DModX) is the distance between observations and a model plane, i.e. residual standard deviation. Hotellings T2 range and DModX are described in more detail in "Multi- and Megavariate Data Analysis: Basic Principles and Applications", L. Ericson, et al., 3rd revised edition, 2013.

The first successful trajectory may be associated with a standard deviation. The confidence criterion may be a function of the standard deviation. For example, the difference between the estimated trajectory and the first successful trajectory may fail the confidence criterion when a distance between a point on the estimated trajectory and a point on the first successful trajectory exceeds a function of the standard deviation associated with the first successful trajectory. In particular, the function of the standard deviation may be multiple standard deviations, e.g. three standard deviations.

The first set of process parameters may include a further process parameter and a corresponding value. The further process parameter may be included in the characterizing process parameters. The corresponding value might not be included in the characterizing process parameters. Accordingly, controlling and monitoring the process may further comprise performing the process using the further process parameter and the corresponding value. The further process parameter may be a control set point. Controlling and monitoring the process may further comprise regulating the process to maintain the control set point (and possibly other control set points) according to the corresponding value (and possibly other values corresponding to the other control set points).

The characterizing process parameters and/or the stored process parameters may include at least one of the following:

- a description of equipment for performing the process,
- a scale of the process,
- a type of the process,
- a name of the product,
- a biological system of the process,
- quality attributes to measure the quality of the product,
- a configuration of the equipment for performing the process,
- concentration of one or more microorganisms, cells, cellular components, enzymes,
- nutrient level (organic, e.g. yeast extract, or inorganic, e.g. trace minerals).

The configuration of the equipment for performing the process may include one or more of the following:

- a target duration of the process,
- a target temperature,
- a stirrer/agitator speed,
- a target pH level,
- a feed rate,
- a target substrate level,
- a target dissolved oxygen level.

The terms stir and agitate, along with stirrer and agitator are used interchangeably in the present application.

The recorded measurements may comprise one or more of the following:

- a current duration of the process (i.e. the length of time that the process has been ongoing),
- a partial pressure of carbon dioxide,
- a cell density,
- a cell viability,
- a substrate concentration,
- a metabolite concentration,
- a time of infection,
- a current temperature,
- a current pH level,
- a current substrate level,
- a current dissolved oxygen level,
- a Near-infrared (NIR) spectrum.

Estimating the trajectory of the process based on the recorded measurements may comprise using multivariate statistical techniques such as projection to latent structures or principal component analysis. Use of principal component analysis to estimate the trajectory of a process is described in more detail in "Multivariate Forecasting of Batch Evolution for Monitoring and Fault Detection", Salvador Munoz, et al., 2002.

Monitoring the process using the first successful trajectory and/or monitoring the process using the second successful trajectory may comprise one or more of the following:

- obtaining a sample of the product being produced by the process,
- analyzing the sample to determine a state of the process. Further, recording measurements of the process may comprise using sensors.

The finishing condition may be met according to one of the following: The process has been performed for a target duration, the steps of an ISA-88 recipe for the process have been completed. The target duration may be a value of at least one of the following: the set of characterizing process parameters, the sets of stored process parameters. The ISA-88 recipe for the process may be associated with the first set of stored process parameters, the second set of store process parameters, or a further set of stored process parameters that has been determined from the stored sets of process parameters according to a similarity comparison, as described above.

Use of an ISA-88 recipe in the context of a batch process is further described in "Batch Control from a User's Perspective", Larry Lamb, June 2000.

The process may be characterized as one or more of the following: chemical, biological, fermentative, biotechnological, pharmaceutical, biopharmaceutical. The process may be batch or semi-batch. When the process is semi-batch, the process may be fed-batch.

Controlling and monitoring the process using the second successful trajectory (and optionally, the second set of process parameters) may comprise recording further measurements of the process and revising the estimated trajectory of the process based on the further recorded measurements. In particular, the trajectory of the process may be estimated based on all measurements recorded for the duration of the process. Controlling and monitoring the process using the second successful trajectory may further comprise comparing the revised trajectory of the process with the second successful trajectory. The comparison may be carried out similarly to the comparison of the estimated trajectory with the first successful trajectory.

When a difference between the revised trajectory and the second successful trajectory fails a further confidence criterion, controlling and monitoring the process using the second successful trajectory may further comprise determining whether a third set of process parameters from the stored sets of process parameters has a greater degree of similarity to the set of characterizing process parameters, the recorded measurements and the further recorded measurements than either the first set or the second set of process parameters. Accordingly, when the third set of process parameters is determined, the method may further comprise controlling and monitoring the process using a third successful trajectory associated with the third set of process parameters.

The further confidence criterion may be a function of a standard deviation of the second successful trajectory. For example, when a difference between a point on the revised trajectory and a corresponding point on the second successful trajectory exceeds a multiple of the standard deviation (e.g. three standard deviations) from the second successful trajectory, the difference between the trajectories may fail the further confidence criterion.

Further controlling and monitoring of the process may be carried out throughout the duration of the process. In particular, the trajectory of the process may be continually estimated throughout performance of the process and compared to a successful trajectory that is currently being used to control and monitor the process. When a comparison between the estimated trajectory and the successful trajectory currently being used to control and monitor the process results in a difference that fails a confidence criterion based on the successful trajectory currently being used, a new successful trajectory may be identified for use in controlling and monitoring the process based on one of the similarity comparisons described above.

The stored sets of process parameters may include public process parameters that are accessible by other database users and private process parameters that are only accessible by a limited number of users, e.g. only an owner of the private process parameters. Each set of these stored sets of process parameters may be anonymized such that it is not possible to connect one of the stored sets of process parameters to a specific user. It is also possible for users of the database to cause arbitrary process parameters to be made private or inaccessible to other users of the database. In some cases, only numerical descriptions of processes and trajectories associated with the processes may be made available. In other words, a user may upload minimal data to the database. The minimal data may include what is necessary for another user to control and monitor the process, e.g. a numerical description of a process and a successful trajectory associated with the process. Alternatively, users of the database may upload further (possibly anonymized) data beyond the minimal data, but only the minimal data is made public to other users of the database. Only making public minimal data may provide improved data security since it is more difficult to connect the uploaded data to a specific user. This may also make is easier to convince a user to upload data to the database, thereby potentially making the database more useful to other users.

Further data beyond the minimal data may also be made public. For example, a particular platform technology, a description of the process, a scale of the process, a type of the process, a particular cell line, and various control parameters for the process such as targets for a duration, a temperature, a stirring/agitating speed, pH, and dissolved oxygen. Making these further parameters public to other users of the database may have the advantage of facilitating control and monitoring of the process. For example, when a specific platform (e.g. cell line, medium) is known then differences in platform can be compensated for or the platform can simply be duplicated.

Uploading additional data beyond the minimal data (e.g. all data associated with a particular process), such that the additional data is not made public, may have the advantage that the user does not need local storage and that all the data can be accessed by different users within the same organization.

Numerical values of the public process parameters may be limited to numerical descriptions of the respective processes. In other words, a stored set of process parameters may include only one numerical value that is public, i.e. a numerical description of the respective process controlled by the stored set of process parameters.

The physical storage of the database may span multiple servers and/or geographical locations. The storage of the database may be managed by a hosting company.

According to another aspect, a computer program product is provided. The computer program product comprises computer readable instructions, which, when loaded and executed on a computer system, cause the computer system to perform operations as described above. The computer program product may be tangibly embodied in a computer readable medium.

According to yet another aspect a computer system is provided. The computer system may be operable to control and monitor a process to produce a chemical, pharmaceutical, or biotechnological product. The computer system comprises a database, at least one control device, and process equipment. The database is configured to store sets of process parameters to control and monitor respective ones of a plurality of processes performed in order to produce products. Each of the stored sets of process parameters is associated with a successful trajectory of a respective one of the processes performed according to the respective set of process parameters. Each successful trajectory is a time based profile of measurements recorded during performance of the respective process. The database is configured to receive a set of characterizing process parameters that characterize the process. A processor associated with the database is configured to identify a first set of process parameters from the stored sets of process parameters. The first set of process parameters has a specified degree of similarity to the set of characterizing process parameters. The first set of process parameters is associated with a first successful trajectory.

The control device may be part of a control system (i.e. a process control system including one or more control devices or a plurality of control devices.

The control device is configured to control and monitor the process using the first set of process parameters and/or the first successful trajectory. The controlling and monitoring may be carried out while the process is performed using the process equipment. In order to control and monitor the process using the first successful trajectory, the control device may include sensors configured to record measurements of the process. The control device is configured to estimate a trajectory of the process based on the recorded measurements.

The system may also be configured as follows.

The control device may be further configured to compare the estimated trajectory with the first successful trajectory.

When a difference between the estimated trajectory and the first successful trajectory fails a confidence criterion, the control device may be configured to cause the database to compare the recorded measurements and the set of characterizing process parameters to a plurality of the stored sets of process parameters.

The database may be further configured to determine, based on the comparison, whether a second set of process parameters from the plurality of stored sets of process parameters has a greater degree of similarity to the set of characterizing process parameters and the recorded measurements than the first set of process parameters.

When the second set of process parameters is determined, the control device may be further configured to control and monitor the process using a second successful trajectory associated with the second set of process parameters. When a finishing condition is met, the control device may be configured to determine that the process is complete.

The subject matter described in this application can be implemented as a method or on a device, possible in the form of one or more computer program products. The subject matter described in the application can be implemented in a data signal or on a machine readable medium, where the medium is embodied in one or more information carriers, such as a CD ROM, a DVD ROM, a semiconductor memory, or a hard disk. Such computer program products may cause a data processing apparatus to perform one or more operations described in the application.

In addition, subject matter described in the application can be implemented as a system including a processor, and a memory coupled to the processor. The memory may encode one or more programs to cause the processor to perform one or more of the methods described in the application. Further subject matter described in the application can be implemented using various machines.

Details of one or more implementations are set forth in the exemplary drawings and description below. Other features will be apparent from the description, the drawings, and from the claims.

BRIEF DESCRIPTION OF THE FIGURES

FIG. 6 shows recorded measurements of a process.

DETAILED DESCRIPTION

In the following text, a detailed description of examples will be given with reference to the drawings. It should be understood that various modifications to the examples may be made. In particular, one or more elements of one example may be combined and used in other examples to form new examples.

Figure 1:
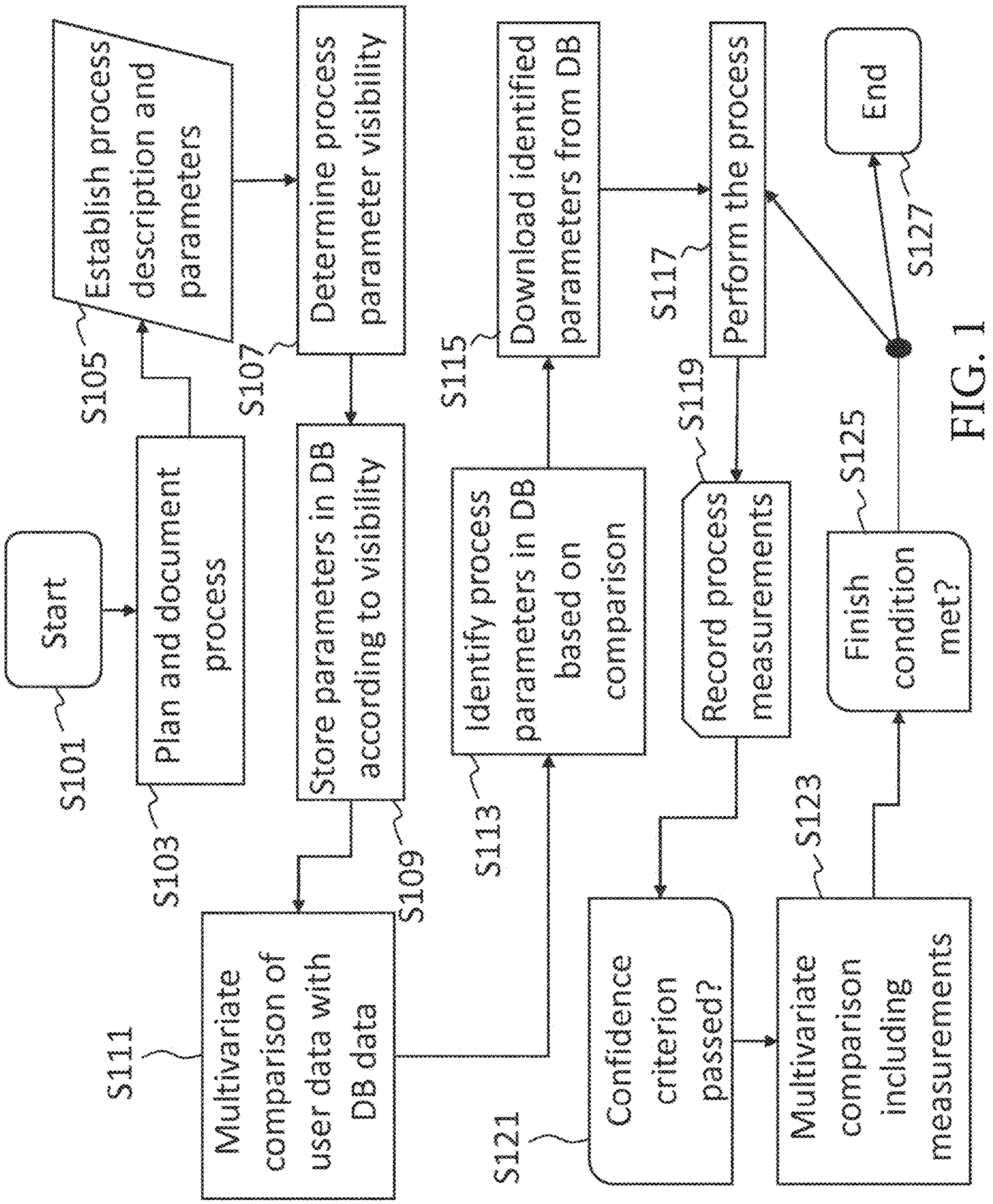
FIG. 1 shows a method of controlling and monitoring a process to produce a chemical, pharmaceutical, or biotechnological product.

FIG. 1 shows a flow chart depicting steps of a computer implemented method of controlling and monitoring a process to produce a chemical, pharmaceutical, or biotechnological product.

FIG. 1 is described in the context of an upstream biopharmaceutical process. However, techniques described in the present application are also applicable for other types of biopharmaceutical processes including harvesting, downstream processes, and drug product processing processes. The techniques of the present application may be applied to any industrial process characterized by correlated data, which may be obtained by recording measurements during the course of the process. Techniques of the present application may be particularly useful in the context of processes performed using process analytical technology (PAT). Process analytical technology is discussed in "Process analytical technology (PAT) for biopharmaceutical products", A. S. Ratore, et al., 18 May 2010.

In addition, techniques described in the present application may be particularly useful for processes in which multivariate data analysis (e.g. of recorded measurements) is carried out. Further, measurement of the quality of the product produced by the process may be laborious and time consuming (e.g. requiring extensive analysis and testing). Accordingly, it may be desirable to estimate the quality of the product produced by the process while the process is still being carried out. Based on the estimation, the process can be controlled and monitored so that the resulting product is more likely to meet specified quality attributes.

The method begins at step S101.

At step S103, a plurality of processes may be planned and documented. The processes may be documented as recipes for use in process control. For example, recipes conforming to the ISA-88 standard (discussed above) may be used.

At step S105, a description and process parameters may be established for each process. Process parameters may also be referred to as variables or process variables. Process parameters may describe the process and specify how the process is executed. Examples of process parameters are as follows:

a. Name of the process b. Description of the process c. Platform technology or biological system (e.g. Cellca cell line, Cellca medium, supplements for the medium)
d. Description of process equipment (e.g. reactor, sensors or other measuring devices, software)
e. Scale of the process (e.g. capacity of the reactor in liters)
f. Batch number
  i. The process
  ii. Components used for the batch
g. Date
h. Type of process
  i. Type of product (e.g. monoclonal antibody, vaccine, microbe)
  ii. Process operation (e.g. batch, fed batch, continuous)
i. Cell line or stem
j. Medium (e.g. powdered, liquid concentrate)
k. Critical Quality Attributes (CQA) and quality target product profile (QTTP), e.g. product concentration, glycosylation, aggregation
l. critical process parameters (CPP)
  i. process duration
  ii. temperature
  iii. stirring speed
  iv. pH
  v. dissolved oxygen
  vi. partial pressure of carbon dioxide
  vii. cell density and cell viability
  viii. substrate concentration (e.g. Glucose, Glutamine)
  ix. Metabolite concentration (e.g. ethanol, glycerol)
  x. Feeding strategy (when, how)
  xi. infection time (vaccine)

The parameters specified above are merely examples. Various combinations of process parameters may be used.

Figure 5:
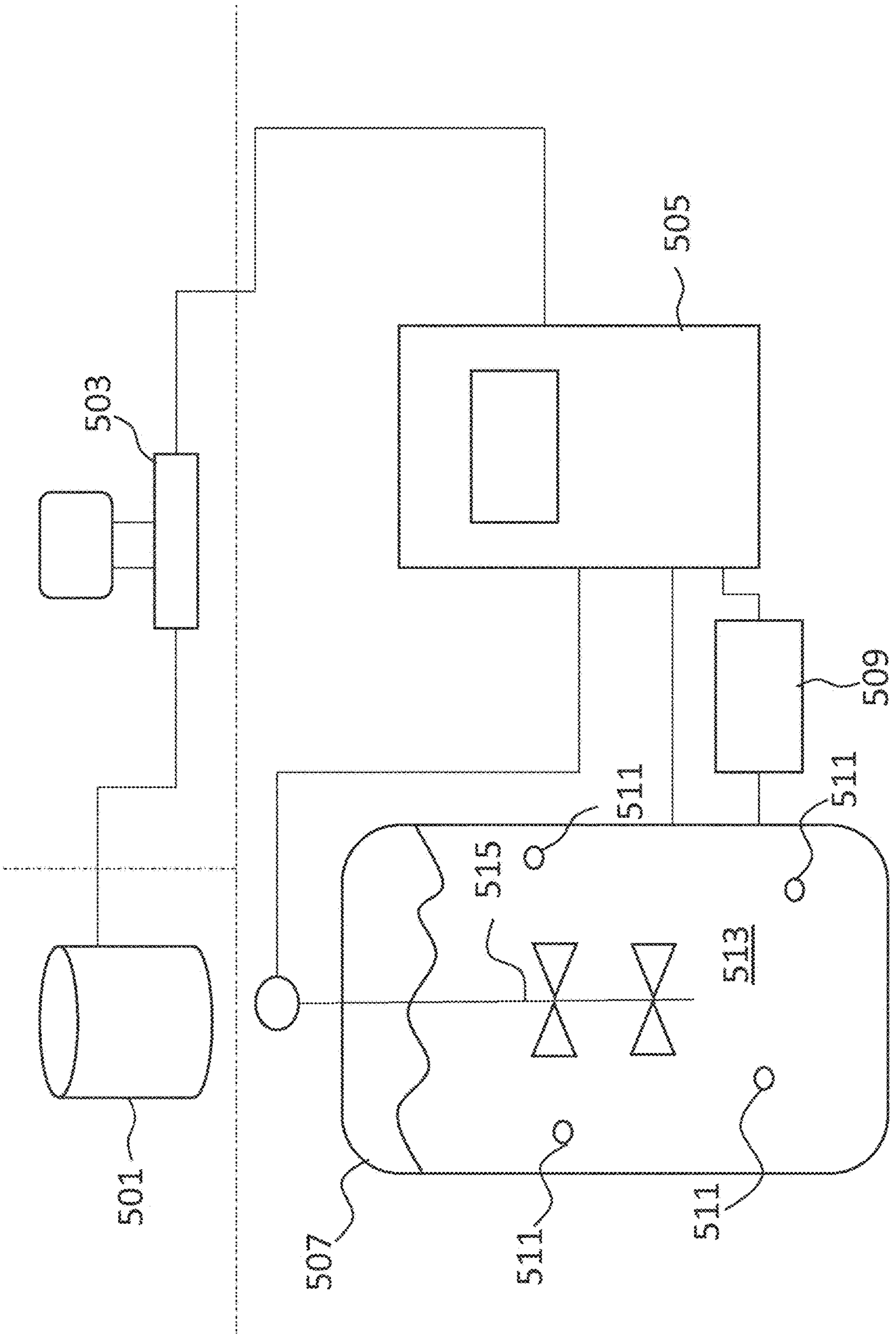
FIG. 5 shows a computer system for controlling and monitoring a process to produce a chemical, pharmaceutical, or biotechnological product.

At step S107, process parameter visibility may be determined. In particular, it may be determined that some of the parameters established in step S105 are public process parameters and others of the parameters established in step S105 are private process parameters. Once the process parameters are stored, public process parameters may be accessible by all users of a database (as shown in FIG. 5) in which the process parameters are stored. In contrast, the private process parameters may be accessible only by a limited number of users. In some cases, the private process parameters may only be accessible by an owner of the process parameters. An identity of a user that stored the process parameters may be excluded from the public process parameters, such that the identity of the user is not visible or determinable from the process parameters.

The critical process parameters described in point l. of step S105 may each be associated with measurements recorded during the course of the process. A numerical description of the process may be derived from the recorded measurements.

Critical process parameters may be a subset of process parameters. Critical process parameters may have or be associated with numerical values. Critical process parameters may be monitored process parameters that has an effect on one or more quality attributes.

For example, the critical process parameters may be described using a plurality of principal components. The numerical description of the process may be calculated as a function of the plurality of principal components. The numerical description of the process may also be referred to as a score of the process. Use of principal component analysis to determine the score of a process is described in "Statistical Process Control of Multivariate Processes", J. F. MacGregor and T. Kurti, 1995. Other multivariate techniques (e.g. partial least squares analysis) may also be used to determine the numerical description of the process.

Accordingly, in some cases only the numerical description of the process may be made public. All other process parameters may be kept private.

In other cases, the following process parameters may be public process parameters: c. platform technology or biological system, d. description of the process equipment, e. scale of the process, h. type of the process, and i. cell line or stem. In addition, the following critical process parameters (under point l.) may be made public: i. process duration, ii. temperature, iii. Stirring/agitating speed, iv. pH, v. dissolved oxygen.

Other process parameters may be kept private, e.g. to improve data security and to prevent other users of the database from determining an owner of the process from the process parameters. In some cases, further process parameters may be made public at the option of the user determining visibility of the process parameters.

At step S109, the process parameters may be stored in the database according to the parameter visibility determined in step S107. The database may be configured such that the private process parameters are not accessible by users of the database other than the owner of the respective process parameters. The process parameters may be stored in the database in sets. Each set of process parameters stored in the database may include public process parameters and private process parameters. The terms public and private describe the visibility or accessibility of the process parameters to users of the database other than the owner of the process parameters. By storing the process parameters in the database according to visibility, the process parameters may be anonymized. Accordingly, if a set of process parameters is retrieved from the database by a user other than the owner of the set of process parameters, then it may be difficult or impossible for the user to determine the owner of the process parameters or to derive private process parameters from the public process parameters. However, the public process parameters may be accessible to all users of the database and may be useful for controlling and monitoring a process to produce a chemical, pharmaceutical, or biotechnological product. In addition, a successful trajectory may be associated with each set of process parameters. The successful trajectory associated with a set of process parameters may be a time base profile of measurements recorded during performance of a process performed according to the set of process parameters.

At step S111, a user of the database may decide to perform a process. The process (or a statistically similar process) may have already been performed by at least one of the other users of the database.

For example, the user may decide to optimize a biopharmaceutical process with the goal of producing a monoclonal antibody in a Chinese Hamster Ovary (CHO) cell line in a bioreactor (e.g., as shown in FIG. 5). The user may determine to perform the process at a particular scale, e.g. 100 liters. This may be the first time that the user has cultivated the monoclonal antibody at this scale and in a Chinese hamster ovary.

A goal of carrying out the process may be to produce a biopharmaceutical product in the optimal product concentration and quality using the CHO cell line, a particular medium and other specified characterizing process parameters. Accordingly, the user has already determined to produce a particular product conforming to specified quality attributes and has access to process equipment (e.g. the bioreactor), the cell line, and the medium in order to reach this goal. However, the user may not know the optimal way to produce the product (i.e. the monoclonal antibody) meeting the quality attributes, or what kind of measurements to expect during a successful run of the process. For example, the user may be uncertain regarding the duration of the process, temperature settings at different stages of the process, or the substrate concentration at different stages of the process. Accordingly, the user may connect to the database and may send a set of characterizing process parameters that characterize the process to the database. These characterizing process parameters may be received at the database at step S111.

A multivariate comparison may be carried out in order to identify a first set of process parameters from the set of stored process parameters. The comparison may involve comparing the characterizing process parameters with sets of process parameters stored in the database at step S109.

As an example, the characterizing process parameters may be compared with all the sets of process parameters stored in the database. Alternatively, the set of characterizing process parameters may be compared with sets of stored process parameters until a set of process parameters is identified from the stored sets of process parameters. In both cases, the identified set of process parameters may have a specified degree of similarity to the set of characterizing process parameters.

The characterizing process parameters received at step S111 may correspond to one of the sets of stored process parameters stored in the database at step S109. However, it may be that values of the critical process parameters that are included in the sets of stored process parameters are not included in the set of characterizing process parameters. In other words, the user may be unaware of appropriate values for at least one of the critical process parameters. In particular, the user may be unaware of values for the process duration, the process temperature, the stirring/agitating speed, the pH, the dissolved oxygen level, the cell density, the cell viability, and other critical process parameters for the process. The process may have more or different critical process parameters than those listed.

At step S113, the first set of process parameters may be identified from the stored sets of process parameters based on the comparison carried out at step S111. The first set of process parameters has the specified degree of similarity to the set of characterizing process parameters. The first set of process parameters is associated with a first successful trajectory.

At step S115, the set of stored process parameters identified in step S113 along with the first successful trajectory may be downloaded from the database. In particular, the public parameters of the stored process parameters may be downloaded from the database. The private parameters of the stored process parameters might not be accessible. In some cases, the downloaded parameters may be limited to text based values (e.g. description of the process and type of product) and a numerical description of the process derived from recorded measurements associated with the critical process parameters. In other cases, further process parameters may have been made public and these parameters along with their associated values may be downloaded at step S115. Various combinations of process parameters may be made public, for example, as discussed in conjunction with step S107. As another example, set points for a plurality of the critical process parameters (e.g. the critical process parameters identified in step S105) may be downloaded from the database.

In addition to the downloaded parameters, the first successful trajectory, a recipe conforming to the ISA-88 standard, and values for the critical quality attributes discussed in step S111 may also be downloaded.

Each set point (also referred to as a control set point) may be understood as a target value for control of the process. For example a temperature set point may be target temperature for the process. A control device may be used to regulate the process according to the set points.

At step S117, performance of the process may begin. Performance of the process may include controlling and monitoring the process using the first successful trajectory. During performance of the process, process data may be continually generated. The process data may be associated with process parameters.

At step S119, measurements of the process may be recorded. In particular, the process data generated by the process may be measured using measurement devices (e.g. sensors) and recorded or stored.

A trajectory of the process may be estimated based on the recorded measurements. Estimating the trajectory of the process may include determining numerical descriptions of process measurements at predetermined intervals and plotting a curve connecting the numerical descriptions of the measurements. Estimating the trajectory of the process may also include estimating how the process will behave in the future. For example, if the process has been performed for 15 seconds estimating the trajectory of the process may comprise approximating behavior or output of the process for a specified duration or until the process is complete. Estimating future behavior of the process (i.e. forecasting) may be carried out using principal component analysis, as described above. Other multivariate statistical techniques for estimating the trajectory of the process or forecasting the trajectory of the process may also be used.

At step S121, the estimated trajectory may be compared with the first successful trajectory. Comparing the estimated trajectory with the first successful trajectory may involve determining whether a difference between the estimated trajectory and the first successful trajectory passes or fails a confidence criterion.

Whether the difference between the estimated trajectory and the first successful trajectory fails the confidence criterion may be determined based on a standard deviation associated with the first successful trajectory. For example, the first successful trajectory may be the mean of multiple trajectories. Each of the multiple trajectories may be associated with a batch of the process corresponding to the first successful trajectory. Accordingly, the confidence criterion may be understood as an upper and lower interval around the first successful trajectory. The intervals may be a function of the standard deviation of the first successful trajectory. For example, the higher interval may be +3 standard deviations from the first successful trajectory and the lower interval may be −3 standard deviations from the first successful trajectory. Other functions of the standard deviation of the first successful trajectory are also possible. If a point on the estimated trajectory falls outside the higher or lower interval, the difference between the estimated trajectory and the first successful trajectory may fail the confidence criterion.

Alternatively, the first successful trajectory may be implemented as the trajectory for a single successful batch or a single successful process. Accordingly, the difference between the estimated trajectory and the first successful trajectory may fail the confidence criterion when a point on the estimated trajectory is a specified distance from the first successful trajectory.

It may be that the difference between the estimated trajectory and the first successful trajectory only fails the confidence criterion when multiple points on the estimated trajectory are the specified distance from the first successful trajectory. For example, each trajectory may be a plot of numerical descriptions of measurements recorded for the respective process over time. If the numerical description of measurements on the estimated trajectory at a particular time differs from the numerical description of measurements on the first successful trajectory at the same time (i.e. measured in seconds from the start of the respective process) by a certain percentage, (e.g. 5% or 10%) the difference between the estimated trajectory and the first successful trajectory may fail the confidence criterion.

Step S123 may be carried out if the confidence criterion fails. At step S123, a comparison of the recorded measurements and the set of characterizing process parameters to a plurality of the stored sets of process parameters may be carried out. The comparison may be a multivariate comparison (i.e. a comparison of parameters, parameter values and measurements using multivariate statistical techniques) to determine statistical similarity between the process being performed and the processes corresponding to the stored sets of process parameters in the database.

Accordingly, based on the comparison, it may be determined whether a second set of process parameters from the plurality of stored sets of process parameters has a greater degree of similarity to the set of characterizing process parameters and the recorded measurements than the first set of process parameters. In some cases, the plurality of stored sets of process parameters may include every stored set of process parameters other than the first set of process parameters. In other cases, the plurality of stored sets of process parameters may be limited to sets of candidate process parameters identified from the stored sets of process parameters via text analysis of text values of the characterizing process parameters or based on user input. The sets of candidate process parameters may be a proper subset of the sets of stored process parameters. If a second set of process parameters having a greater degree of similarity to the characterizing process parameters and the recorded measurements than the first set of process parameters cannot be determined, an alarm may be sounded so that the user can decide how to proceed further. Alternatively, a different database storing sets of process parameters may be automatically selected and queried.

The comparing of the recorded measurements and the set of characterizing process parameters to the plurality of the stored sets of process parameters may be carried out by determining a plurality of principal components from the characterizing process parameters and the recorded measurements. The determination of principal components may be carried out according to principal component analysis, as discussed above.

A characterizing numerical description of the process may be calculated as a function of the plurality of principal components. The characterizing numerical description may be referred to as a score. The characterizing numerical description may also be calculated according to principal component analysis. In addition, instead of principal component analysis, other multivariate statistical techniques may be used, e.g. partial leased squares with discriminant analysis. Further, the SIMCA software from Umetrics may also be used.

The process may be continually performed (as well as controlled and monitored) in the steps subsequent to step S117 until it is determined that a finishing condition is met. A determination as to whether the finishing condition is met is carried out at step S125. When the finishing condition is met, a determination is made that the process is complete and the process ends at step S127. If the finishing condition is not met, the method returns to step S117 and the process continues to be performed. During performance of the process, recorded measurements of the process may be continuously uploaded to the database. Visibility of the recorded measurements may be determined according to the procedure discussed in step S107. For example, each recorded measurement may be associated with a process parameter. Accordingly, visibility of the recorded measurement corresponding to a process parameter may be determined according to the visibility of the process parameter. In some cases, only a numerical description of the process or numerical descriptions of the measurements at particular points in time during the process may be visible.

When the process ends at step S127, the set of characterizing parameters and recorded measurements corresponding to the process may be marked as complete in the database. Once the process is marked as complete, a successful trajectory may be derived from the recorded measurements and the process parameters may be made available to other users of the database as one of the sets of stored process parameters, along with the associated successful trajectory. The availability of the process parameters may be determined according to visibility settings, as discussed above. In some cases, only parameters and trajectories associated with processes marked as complete may be available or visible to other users of the database. This may have the advantage of making it more likely that controlling and monitoring of new processes is only carried out using successful trajectories associated with completed processes. Alternatively, it may be possible for users to access data associated with incomplete processes. This may have the advantage of making more useful data available to users of the database faster.

The method of controlling and monitoring a process to produce a chemical, pharmaceutical, or biotechnological product as described in the context of FIG. 1 may have the advantage of enabling the process to be evaluated and adjusted while being carried out. This may result in fewer failed processes (i.e. processes that fail to produce products meeting quality attributes). Further, it may be easier to implement a new process or to scale up a process (e.g. move from a bioreactor with five liters of starting material to a bioreactor with 30 liters of starting material).

Figure 2:
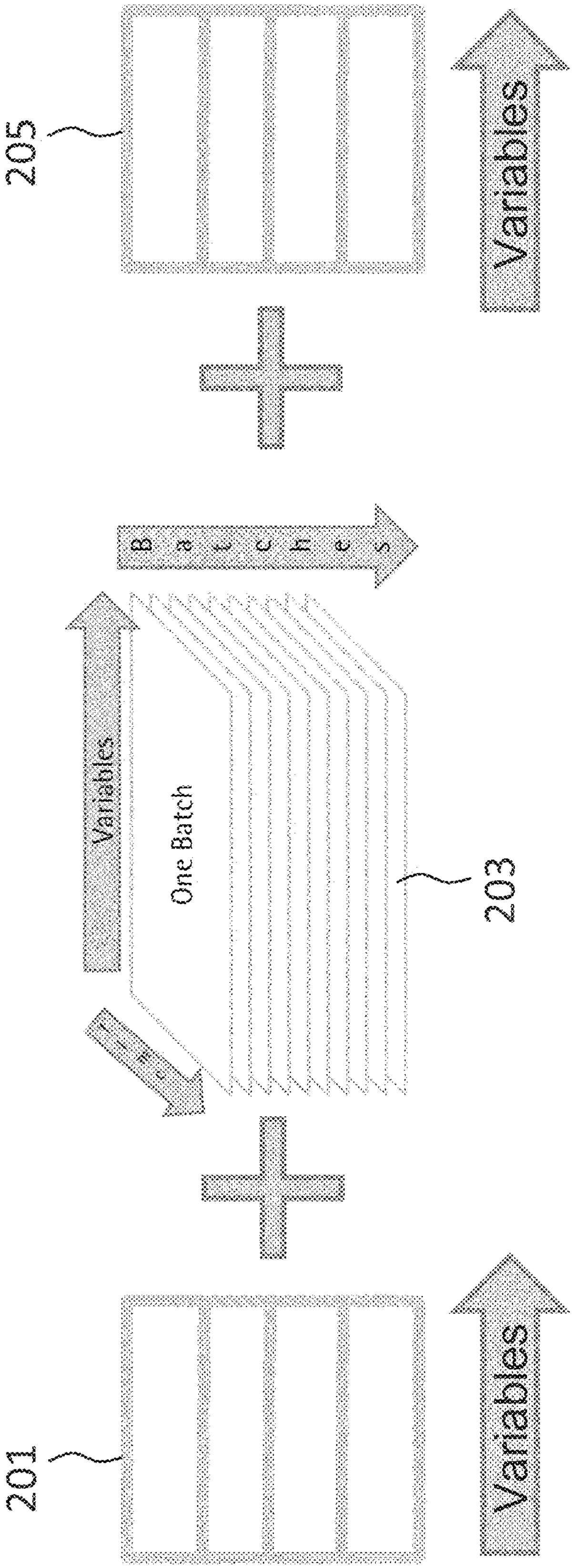
FIG. 2 depicts batch processing including initial conditions and results

FIG. 2 shows the evolution of a process 203 to produce a chemical, pharmaceutical or biotechnological product. In the example of FIG. 2 the process 203 is a biopharmaceutical process and the product is a biopharmaceutical product. In particular, the process 203 is a batch process.

Process parameters 201 specify initial conditions of the process 203. It should be noted that although the description of FIG. 2 is provided in the context of a batch process, the techniques described are also applicable to other types of industrial processes. The process parameters 201 may also be referred to as variables. The process parameters 201 may include a scale having the value 10 liters, a cell system having the value Chinese Hamster Ovary (CHO), a control set point for pH having the value 7.2 and a control set point for dissolved oxygen having the value 80%.

The process parameters 201 may include process metadata and further control set points. In particular, the process metadata may be text values describing the process 203, e.g. cell strain, product name, batch type. The control set points may be used to control or regulate the bioreactor in which the process 203 is performed. The characterizing process parameters and the stored sets of process parameters may also include control set points and process metadata corresponding to the control set points and the process metadata included in the process parameters 201.

In addition, measurements recorded during performance of the process 203 may also correspond to the process parameters 201. Further, the process parameters 201 may also include quality attributes 205, also referred to as offline process parameters. The quality attributes 205 may include critical quality attributes or all the quality attributes 205 may be critical quality attributes. The quality attributes 205 may be used to determine whether the product produced via the process can be used or should be rejected. The quality attributes may include a batch product titer, a viability (i.e. harvest), and a duration. Other quality attributes (as discussed above) may also be included in the quality attributes 205. The product titer may be measured in grams per liter, e.g. 8 grams per liter. The viability may be provided as a percentage, e.g. 90%. The duration may be measured in seconds, minutes, hours, or days, e.g. 17 days.

Figure 3:
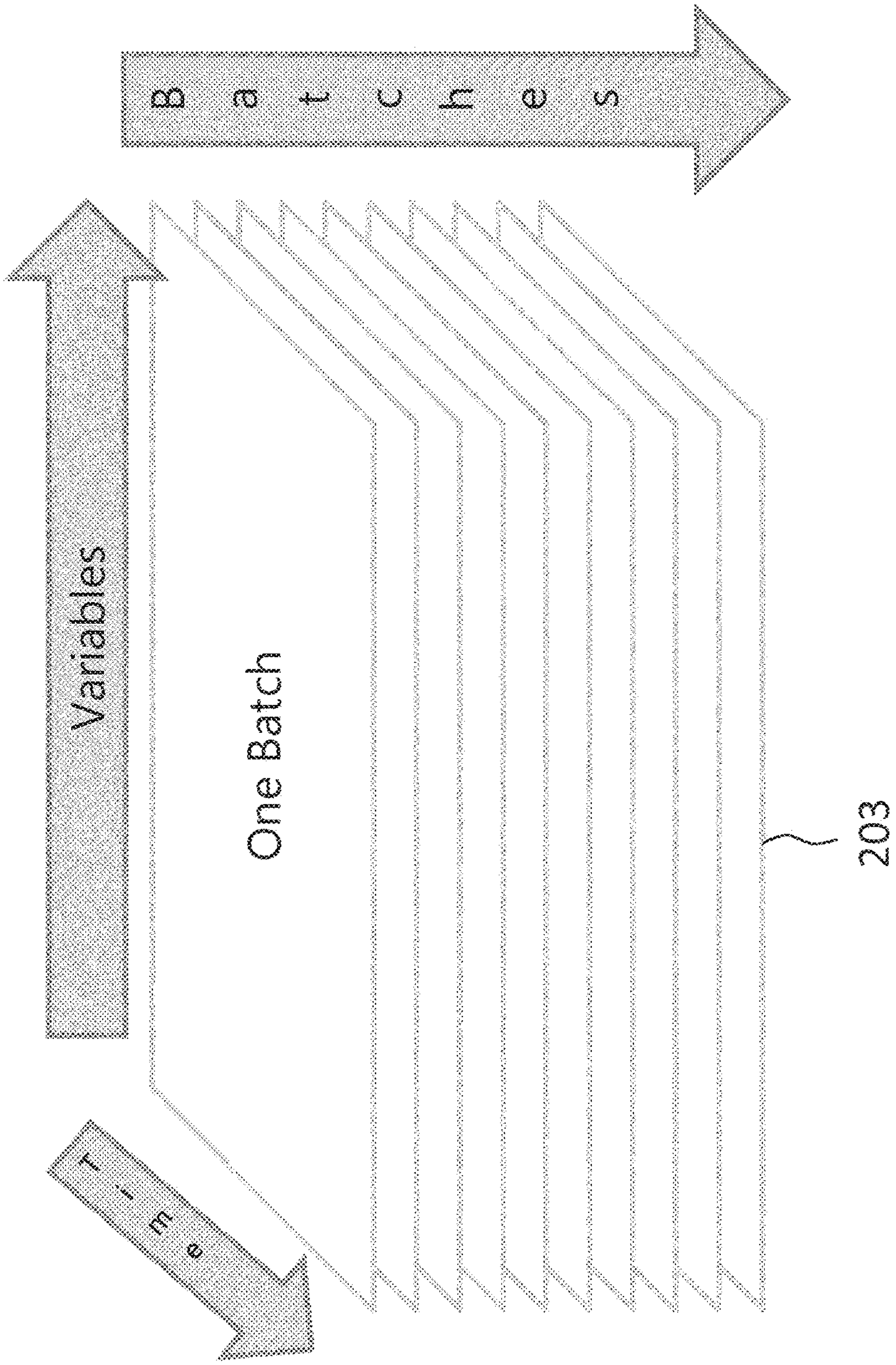
FIG. 3 shows a visualization of batch data stored in a database.

FIG. 3 shows the process 203 in more detail. The process 203 may include multiple batches. Each batch may be performed for the same amount of time and performance of the batch may be controlled and/or characterized by the same process parameters 201. In some cases, each batch may be performed within the bioreactor (as shown in FIG. 5), and the bioreactor may be cleaned in between batches.

Figure 4:
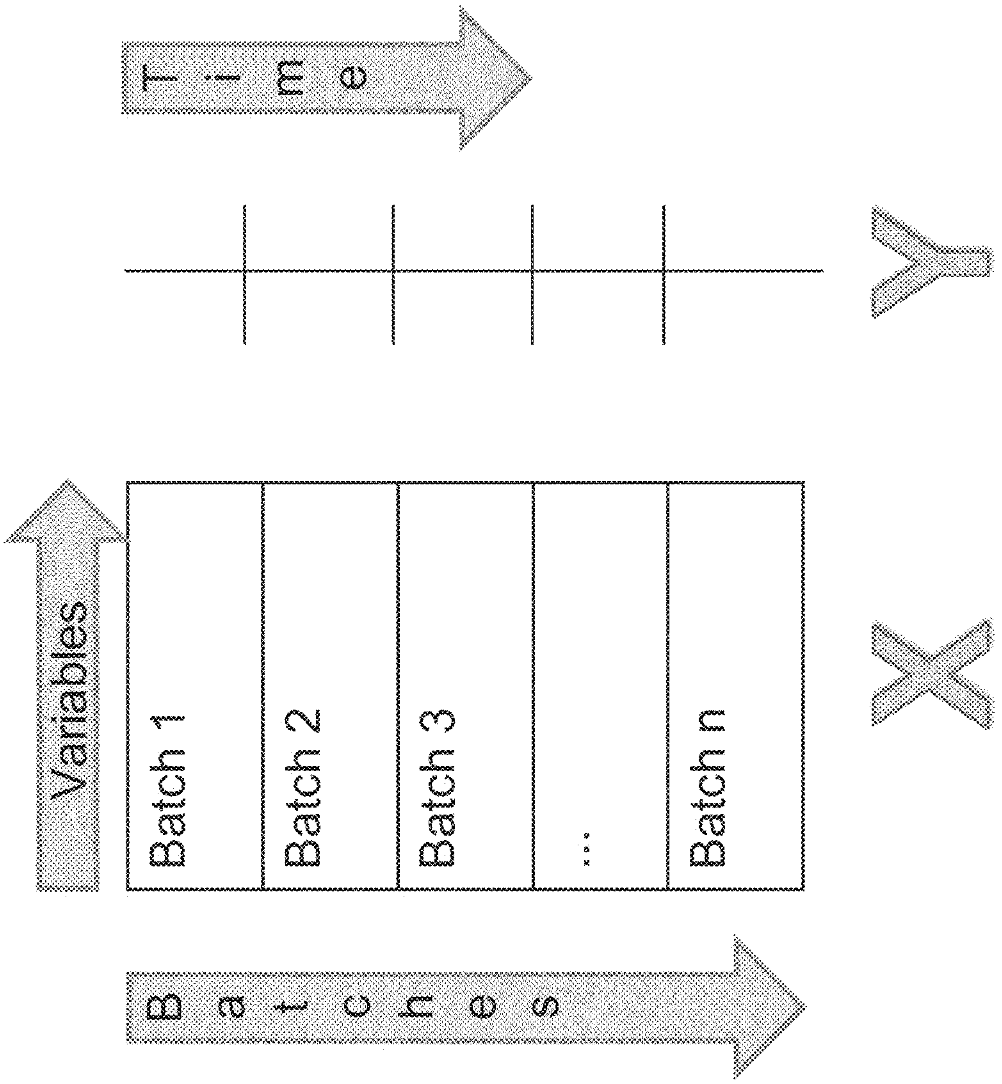
FIG. 4 shows a progression of batch processing according to an implementation.

FIG. 4 shows a visualization of a trajectory of the process 203. The trajectory is a time based profile of measurements recorded during performance of the process 203. The measurements may be recorded over multiple batches of the process 203. Alternatively, the process 203 may consist of one batch or the process 203 may be continuous. In some cases, the trajectory of the process 203 may be numerical descriptions of the recorded measurements of the process over time. Numerical descriptions of measurements may be derived using multivariate statistical techniques, e.g. principal component analysis or partial leased squares. Other multivariate statistical techniques may also be used, e.g. other techniques available in the SIMCA software described above.

FIG. 5 shows devices and equipment that may be used in the method of controlling and monitoring the process 203.

In particular, a database 501 may be provided. The database 501 stores sets of process parameters to control and monitor respective ones of a plurality of processes performed in order to produce products, as described above. The database 501 may be hosted by a service provider, possibly on a virtual machine, and may be accessible by various users from multiple organizations, possibly located in a variety of different geographic locations around the world.

A process control system may also be provided. The process control system may include a process control device 503, a local control device 505 and possibly further control devices. The process control device 503 may be operable, possibly in conjunction with other control devices in the process control system, to control and monitor the process 203 using the first successful trajectory.

In particular, the process control device 503 may be operable to receive recorded measurements of the process 203. The process control device 503 may also be operable to estimate a trajectory of the process 203 based on the recorded measurements and compare the estimated trajectory with the first successful trajectory. The process control device 503 may be further operable to perform various further comparisons (e.g. similarity comparisons) and determinations. More specifically, when the difference between the estimated trajectory and the first successful trajectory fails the confidence criterion, the process control device 503 may be operable to compare the recorded measurements and the set of characterizing process parameters to a plurality of stored sets of process parameters. The process control device 503 may be further operable to determine, based on the comparison, whether a second set of process parameters from the plurality of stored sets of process parameters has a greater degree of similarity to the set of characterizing process parameters and the recorded measurements than the first set of process parameters. The process control device 503 may also be operable to control and monitor the process 203 using a second successful trajectory associated with the second set of process parameters when the second set of process parameters is determined. The process control device 503 may be also be operable to determine when a finishing condition is met and to determine that the process 203 is complete when the finishing condition is met.

The process control device 503 may be located in a control room. The process control device 503 may be connected to the database 501, possibly via a secure connection. Data passed from the process control device 503 to the database 501 may be cryptographically protected, e.g. encrypted. The database 501 may be located in a location that is geographically distant (e.g. on another continent) from the process control device 503.

The process control device 503 may be connected to the local control device 505. The local control device 505 and the additional components depicted in FIG. 5 may be located in a production facility. The local control device 505 and the process control device 503 may be located in different rooms of the same facility or in different buildings on a corporate campus. The local control device 505 may include a control loop feedback mechanism, e.g. a proportional integral derivative controller (PID controller). The local control device 505 may be connected to a bioreactor 507 and an analyzer 509. The bioreactor 507 may include a plurality of cells 511 in a medium 513. The bioreactor 507 may also include an agitator 515 (i.e. a stirrer). The analyzer 509 may also be considered a control device.

The bioreactor 507 may be implemented as a 10 liter Biostat C bioreactor, manufactured by Sartorius AG, including control and inline measurement capability. In particular, the bioreactor 507 may be capable of controlling and measuring the following: temperature, pH, dissolved oxygen concentration, cell density of the cells 511, near infrared spectroscopy. The bioreactor 507 may be capable of recording a variety of measurements using the measurement devices mentioned above and further measurement devices. The bioreactor 507 may be capable not only of fermentation but also of developing mammalian cell cultures. In conjunction with the local control device 505, the bioreactor 507 may be capable of performing various forms of inline measurement and analysis, in which the medium 513 is measured while remaining in the bioreactor.

In addition, the analyzer 509 may be used to perform atline or online analysis. In particular, a probe may remove a sample of the medium 513 from the bioreactor in order to perform and record measurements. The results of the measurements may be sent from the analyzer 509 to the local control device 505 or the process control device 503. For example, the analyzer 509 may measure the concentration of the substrate glucose or the metabolite lactate. The measurement of the concentration of the substrate glucose and/or the metabolite lactate may be carried out every 12 hours. The analyzer 509 may be capable of performing and recording various other measurements of the process 203.

The local control device 505 may connect to the bioreactor 507 and the analyzer 509 in order to control and monitor the process 203 using the first successful trajectory. Via the control loop feedback mechanism, the local control device 505 may use the recorded measurements of the process 203 and the control set points (possibly provided in the characterizing process parameters, in the first set of process parameters or in the second set of process parameters) in order to control the process 203. In particular, the measurements recorded from the bioreactor 507 may be used to maintain the medium 513 according to the control set points. The process control device 503 may be understood as a supervisory system that receives the recorded measurements of the process 203 and performs multivariate data analysis in order to estimate whether the process 203 will result in the production of a product meeting predetermined quality attributes, e.g. the quality attributes 205.

Further devices may also be used to analyze the medium 513 and determine whether the quality attributes 205 have been met. The quality attributes 205 may include a glycosylation profile and a potency (i.e. biological activity of antibodies). It may be that critical quality parameters can only be measured offline. In other words, measurements of critical quality parameters may not be available until the process 203 is complete.

The database 501 may be a relational database, and object relational database, or an object oriented database. Various database management systems may be used such as Oracle, MySQL, and Microsoft SQL.

Transparent data encryption (TDE) may be used to encrypt database files. Other cryptographic database protection mechanisms may also be used. In order to determine process parameter visibility as discussed in step S107, a discretionary access control policy may be used. Other types of access control policies may also be used in order to ensure that users of the database only have access to public process parameters and that private process parameters are only accessible by a limited number of users or the owner of the corresponding set of stored process parameters.

The database 501 may be accessible from the process control device 503 via the Internet. Communications between the database 501 and the process control device 503 may be secured, e.g. via Internet protocol security (IPSEC) or other security protocols. A virtual private network (VPN) may also be used.

The database 501 may be implemented using clustering and/or load balancing in order to ensure a high level of availability and fault tolerance. A registration process may be provided for users to register to use the database 501. The registration process may allow individual persons, work groups, companies, or various types of institutions (e.g. universities) to register to use the database 501. An authentication process for accessing the database 501 may also be established. In particular, two factor authentication may be required to access the database, such that a password plus a code provided to a mobile phone via SMS or a password plus a token are required to access the database. The database 501 may be used to control and monitor the process 203. In particular, the database 501 may be used to optimize pharmaceutical production processes.

According to an example, a user may desire to control and monitor the process 203 using the sufficiently characterized Cellca cell line as a biological system. The Cellca cell line carries the gene for the expression of a monoclonal antibody. A medium, nutrient solution, and supplements corresponding to the Cellca cell line may be used as part of the biological system. Continuing the example, the user may enter the control room in order to use the process control device 503. Accordingly, the user may log in to the process control device 503 in order to prepare a production run and a first batch. The user may enter the following process parameters in the process control device 503:

a. Name of the process
b. Description of process equipment (e.g. a description of the bioreactor 507)
c. Scale of the process: 10 liter reactor
d. Batch number
 i. the process
 ii. the components used
e. Date
f. Type of process
 i. type of product: monoclonal antibody
 ii. process strategy: fed batch
g. Biological system (as described above)
 i. Cellca cell line
 ii. Cellca medium and supplements
h. Critical quality attributes
 i. product concentration
 ii. glycosylation profile
i. Critical process parameters
 i. process duration
 ii. temperature
 iii. stirring speed
 iv. pH
 v. dissolved oxygen
 vi. cell density
 vii. substrate concentration (glucose)
 viii. metabolite concentration (lactate)

According to the example, the critical process parameters may be determined but their values may not be known. The values of the critical cross process parameters may be retrieved from the database. In particular, the values of the critical process parameters may be included in one of the stored sets of process parameters stored in the database 501. After entry of the process parameters specified above, the process control device 503 may connect to the database 501. The connection between the process control device 503 and the database 501 may be a secure connection, e.g. via a VPN or IPSEC. A subset of the parameters entered into the process control device 503 maybe transferred to the database 501. The subset of parameters transferred to the database 501 may be referred to as the set of characterizing process parameters that characterize the process. In the context of the present example, the characterizing process parameters may be as follows:

a. Scale of the process: 10 liter reactor
b. Batch number
 i. components used
c. Type of process
 i. type of product: monoclonal antibody
 ii. process strategy: fed batch
d. Biological system
 i. Cellca cell line
 ii. Cellca medium and supplements
e. Critical quality attributes
 i. product concentration
 ii. glycosylation profile
f. Critical process parameters
 i. process duration
 ii. temperature
 iii. stir speed
 iv. pH v. dissolved oxygen
vi. cell density
vii. substrate concentration (e.g. glucose)
viii. metabolite concentration (e.g. lactate)

The characterizing process parameters are compared with the stored sets of process parameters in order to identify the first set of process parameters, as described above. The first set of process parameters may be identified using multivariate statistical techniques, as discussed above. In addition to the literature discussed above, multivariate statistical techniques relevant to the present application are further described in "A User Friendly Guide to Multivariate Calibration and Classification" T. Nehers, et al., 2002. Also relevant is "Chemometrics", Matthias Otto, 2007.

A goal of identifying the first set of process parameters having the specified degree of similarity to the set of characterizing process parameters is to provide the user with optimal process parameters that are not yet known to the user. Advantageously, the user receives guidance for determining whether recorded measurements of the process are consistent with what they should be and for determining how to control the process so that it results in the production of a viable product, i.e. a product meeting predetermined quality attributes. The guidance is provided in the form of the first successful trajectory associated with the first set of process parameters. In some cases, the first set of process parameters also includes values for control set points for use in controlling the process. Further, the first successful trajectory may be used to ensure that recorded measurements of the process meet a confidence criterion (e.g. they are within a desired interval) such that the process will result in the production of a viable product meeting quality attributes.

Continuing the example, once the first set of process parameters has been identified, the first successful trajectory associated with the first set of process parameters may be transferred from the database 501 to the process control device 503. The first set of process parameters may include public process parameters. In particular, the first set of process parameters may include values for control set points specified in the characterizing process parameters. For example, the first set of process parameters may include values for the following control set points:

i. process duration
ii. temperature
iii. stirring speed
iv. pH
v. dissolved oxygen
vi. cell density
vii. substrate (e.g. glucose) concentration
viii. metabolite (e.g. lactate) concentration The database 501 may also transmit an ISA-88 recipe (as discussed above) to the process control device 503. The ISA-88 recipe may be used to control the process. In particular, the ISA-88 recipe may define a process model consisting of an ordered set of stages, where each stage comprises operations and each operation comprises actions. In addition, the database 501 may transmit values for quality attributes to the process control device 503. The quality attributes themselves may be specified without values as part of the set of characterizing process parameters that characterize the process.

In addition, user comments may be associated with the first set of process parameters stored in the database. The user comments may also be transferred from the database 501 to the process control device 503. The user comments may include suggestions as to how to better measure and control the process. In particular, the user comments may specify further process parameters for use in measuring and controlling the process. For example, the user comments may suggest measuring dissolved carbon dioxide concentration in the bioreactor 507 for the process because control of this particular process parameter has been helpful when performing similar processes. Once this information has been transferred to the process control device 503, performance of the process in the bioreactor 507 may begin. Performance of the process may include controlling and monitoring the process using the first successful trajectory. Before performing the process, the user may prepare the bioreactor 507 by sterilizing the bioreactor 507 and filling the bioreactor 507 with the medium 513. In addition, the user may make necessary connections to the bioreactor 507 to prepare the bioreactor 507 for operation. This may include connecting the analyzer 509 and the local control device 505 to the bioreactor 507.

As the process is being performed, measurements of the process are recorded. In particular, measurements corresponding to process parameters may be recorded inline via the bioreactor and online or atline via the analyzer 509. Based on the recorded measurements, the process control device 503 may estimate a trajectory of the process. The estimated trajectory of the process may be compared with the first successful trajectory. Comparisons of the estimated trajectory with the first successful trajectory may be made throughout performance of the process, as described in the context of FIG. 1.

When the difference between the estimated trajectory and the first successful trajectory fails the confidence criterion, the database 501 may be queried by the process control device 503 in order to determine whether one of the sets of process parameters stored in the database has a greater degree of similarity to the process being performed in comparison to the first set of process parameters. The greater degree of similarity may be determined based on all information regarding the process that is available. In particular, the greater degree of similarity may be determined via a similarity comparison, as discussed above, by comparing the recorded measurements and the set of characterizing process parameters to a plurality of the stored sets of process parameters. The comparison may be a multivariate comparison as discussed in connection with step S123 above. Such multivariate comparisons may generally be carried out with all recorded measurements for the process along with the characterizing process parameters. Accordingly, as more information about the process becomes available during further execution of the process, different sets of stored process parameters may be determined to be the most similar set of stored process parameters to the characterizing process parameters of the process being performed.

When a second set of process parameters from the plurality of stored sets of process parameters is determined to have a greater degree of similarity to the set of characterizing process parameters and the recorded measurements then the first set of process parameters, then a second successful trajectory associated with the second set of process parameters is used to control and monitor the process.

During performance of the process, the process may continually be monitored to determine whether the difference between the estimated trajectory of the process and a current (e.g. first or second) successful trajectory corresponding to a set of stored process parameters passes or fails the confidence criterion. If the confidence criterion fails, an attempt will be made to determine a more suitable set of stored process parameters from the process parameters stored in the database 501. In this context, more suitable means a set of stored process parameters having a greater degree of similarity to the parameters and measurements currently available for the process then the set of stored process parameters and corresponding trajectory currently being used to control and monitor the process.

The multiple database queries carried out during performance of the process may have the advantage of making it possible to take advantage of the latest information in the database 501 and to gradually tailor performance of the process. For example, the first set of process parameters may be selected from among many equally similar sets of stored process parameters. The first set of process parameters may be suitable for initial execution of the process, but after some time, more similar process parameters may be needed in order to ensure that the quality attributes are met. Accordingly, after the process has been performed for some time, there may be more data available for comparison and the second (or third) set of process parameters (each determined according to the similarity comparison) may be much more similar to the process being performed in comparison to the first set of process parameters.

The finishing condition may be determined to be met according to the ISA-88 recipe. In particular, the ISA-88 recipe may specify when the process is complete. Once the process is complete or a batch of the process is complete, the user may harvest the contents of the bioreactor 507 and the monoclonal antibody that is the product being produced. The user may then analyze the product, i.e. the monoclonal antibody in his example, in order to determine whether the specified quality attributes have been met. In particular, the user may analyze the monoclonal antibody in order to determine whether the glycosylation profile and potency of the monoclonal antibody meet criteria in the quality parameters. If the criteria are met, the batch may be marked as successful in the process control device 503. The process control device 503 may then forward the recorded measurements for the process to the database 501. Recorded measurements and parameters of the process may be stored in the database 501 according to an access policy specified by the user, as discussed above in conjunction with step S107.

According to the access policy, some of the process parameters and recorded measurements may be public and accessible by other users, whereas some of the process parameters and recorded measurements may be private and inaccessible. Accordingly, resulting data for the finished process including recorded measurements and process parameters may become a further stored set of process parameters available to other users for controlling and monitoring further processes to produce chemical, pharmaceutical, or biotechnological products.

FIG. 6 shows recorded measurements for a batch of a process to produce a chemical, pharmaceutical or biotechnological product. The process may include multiple batches. Each row shows measurements recorded at different times during performance of the batch. A column 600 shows times during the batch process that are relevant for (e.g. measurement) other columns shown. A column 601 shows the age of the batch in hours. A column 603 shows a temperature control set point. A further column 605 shows temperature measurements of the medium. A further column 607 shows measurements of a stirring speed. Another column 609 shows a pH control set point. Yet another column 611 shows recorded pH measurements. Another column 613 shows a control set point for the partial pressure of Oxygen.

Figure 7:
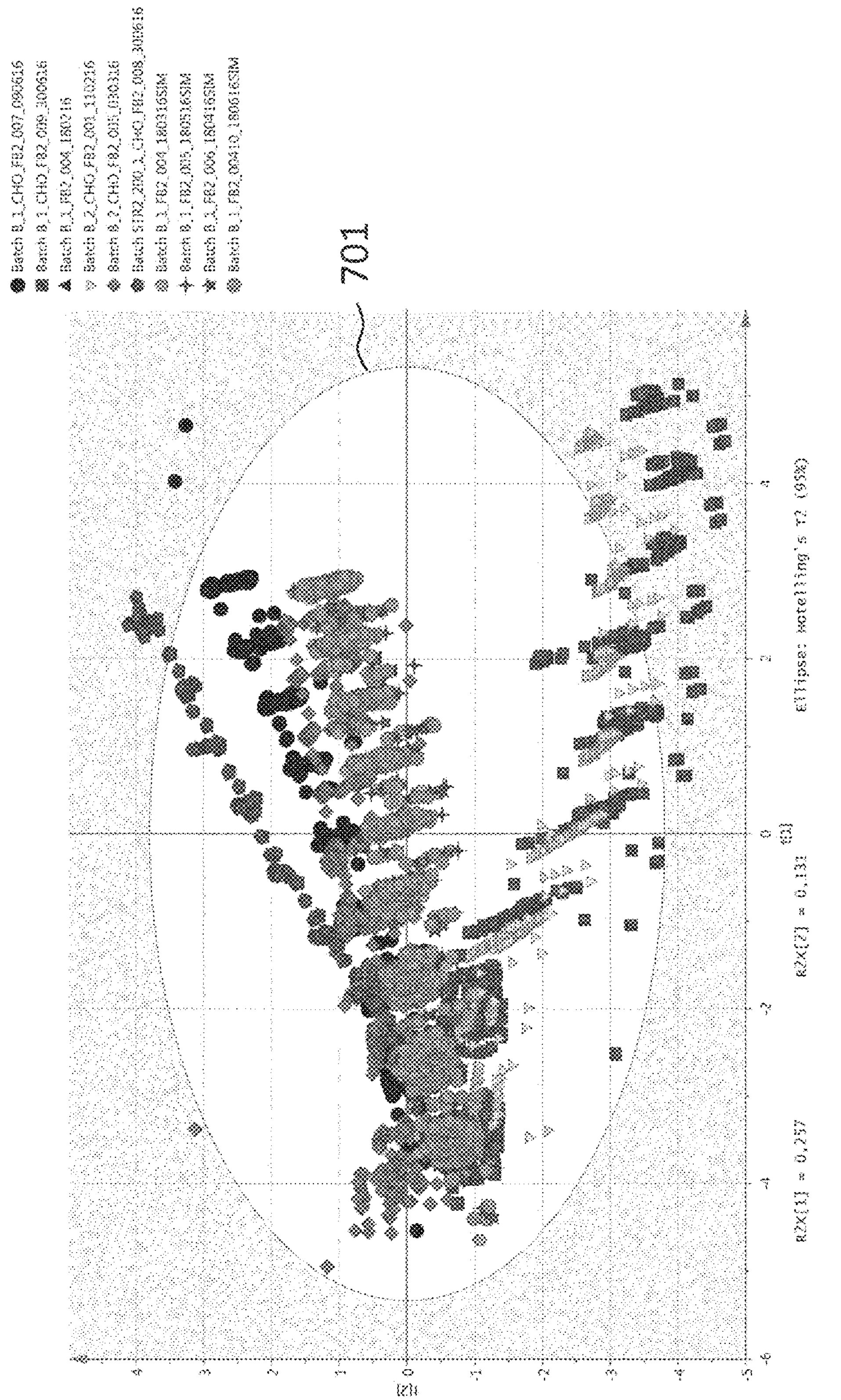
FIG. 7 shows numerical descriptions of batches of a process.

FIG. 7 shows numerical descriptions of measurements for multiple batches plotted throughout the corresponding batches. The batches may be part of a single process or multiple processes. Bad batches (i.e. batches that did not meet the specified quality parameters) corresponding to unsuccessful trajectories may have a number of points shown outside an ellipse 701. Good batches corresponding to successful trajectories may show some or all points plotted within the ellipse 701. The batches may be for a fed batch process and one of the process parameters may be the Cellca CHO cell line.

Figure 8:
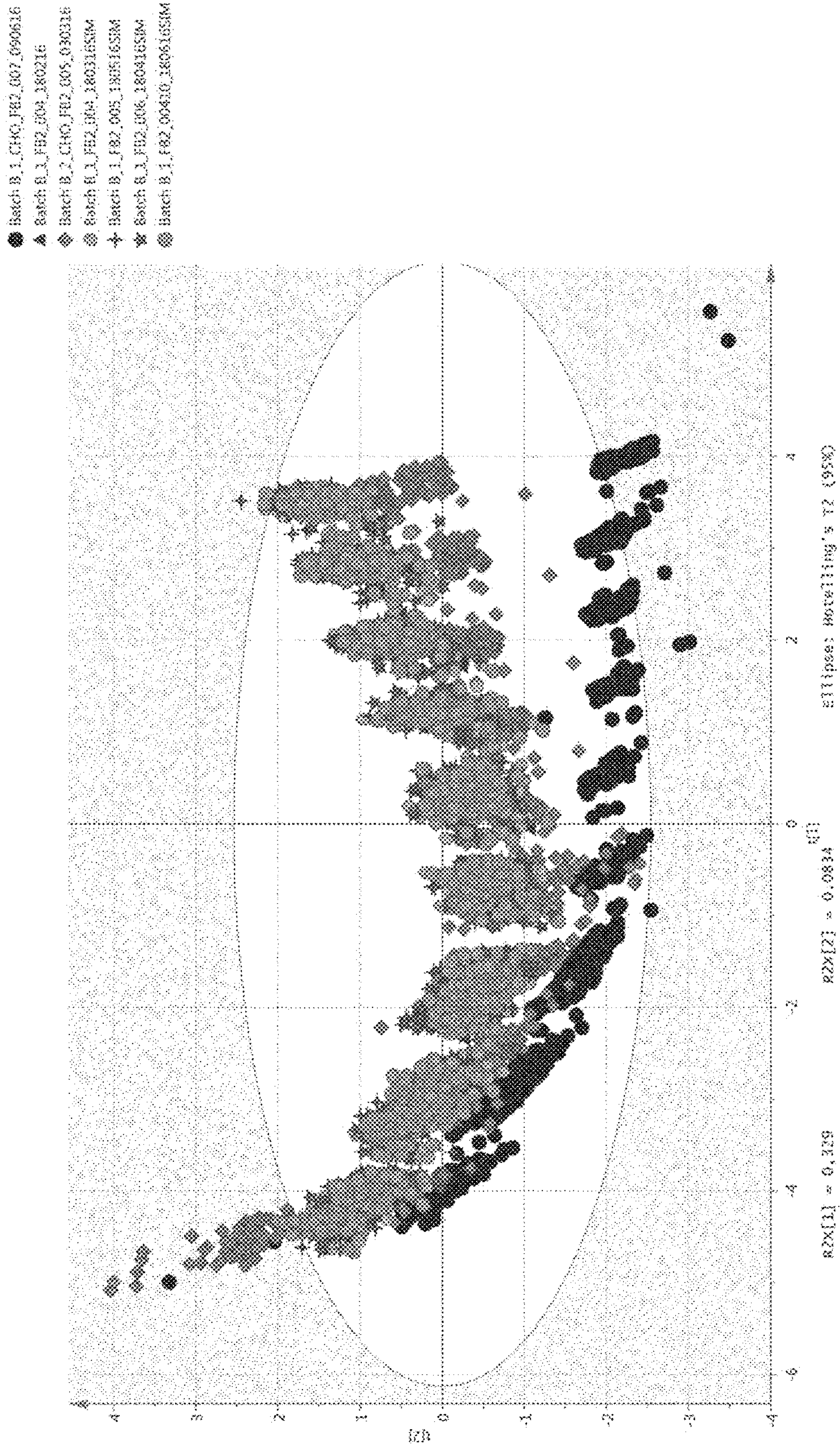
FIG. 8 shows numerical descriptions of batches of the process after the numerical descriptions of batches that did not meet quality attributes have been removed.

FIG. 8 shows another scatter plot of numerical descriptions of measurements for various batches taken over time. Each of the batches may correspond to a process. In the scatter plot of FIG. 8, the bad batches corresponding to unsuccessful trajectories (shown in FIG. 7) have been eliminated from the scattered plot.

Figure 9:
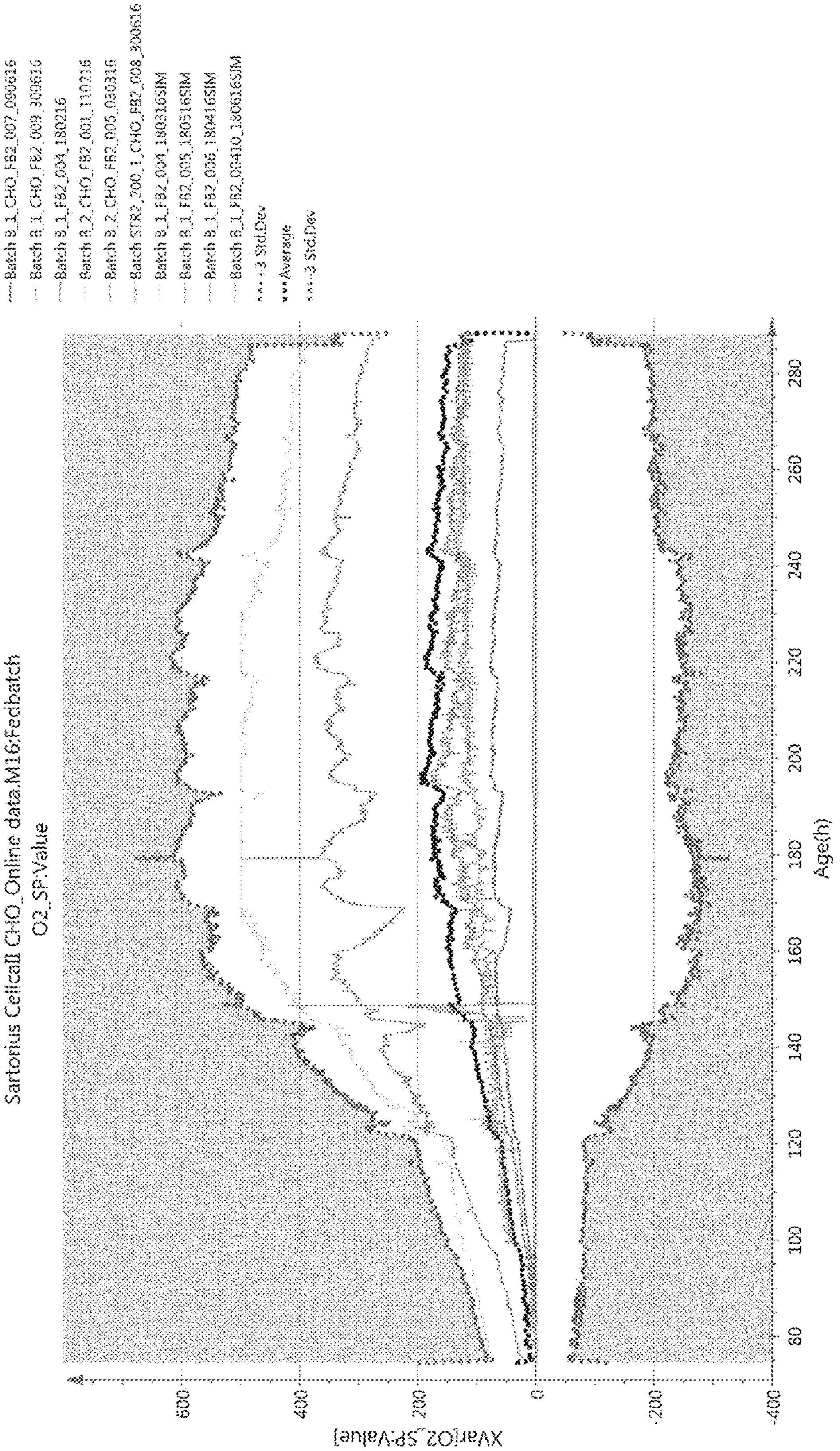
FIG. 9 shows trajectories of batches of the process.

FIG. 9 shows batch control charts (i.e. a trajectories) for recorded measurements associated with a single process parameter for a fed batch process plotted over time. In addition, an average for all the batches is plotted along with a confidence interval three standard deviations higher and three standard deviations lower than the average.

Figure 10:
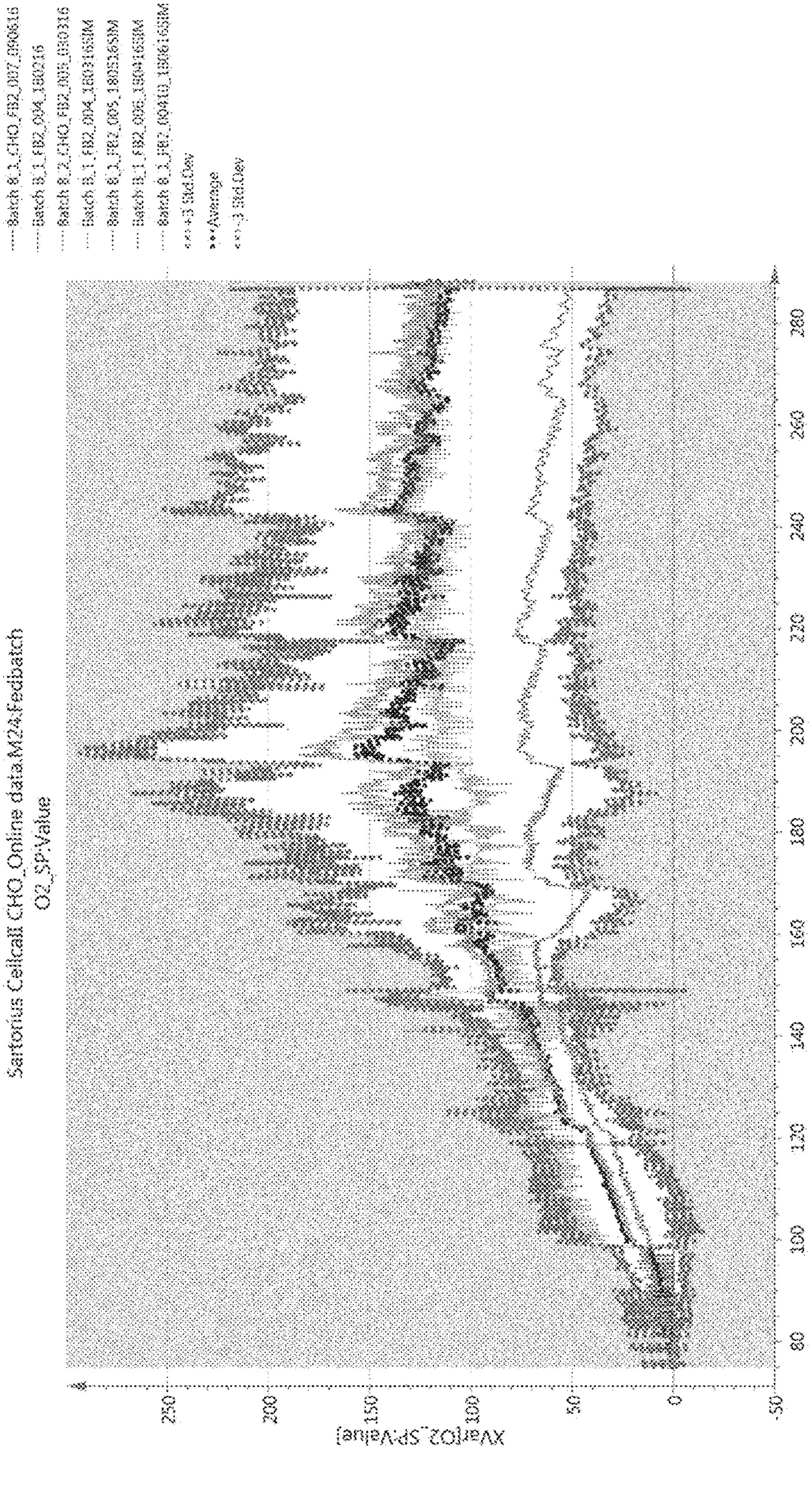
FIG. 10 shows trajectories and a confidence interval for batches of the process after the removal of deviant trajectories.

FIG. 10 shows trajectories for batches of the process after removal of deviant trajectories corresponding to bad batches. In addition, an average for all the batches is plotted along with a confidence interval similar to the one for FIG. 9, i.e. three standard deviations higher and three standard deviations lower than the average.

Figure 11:
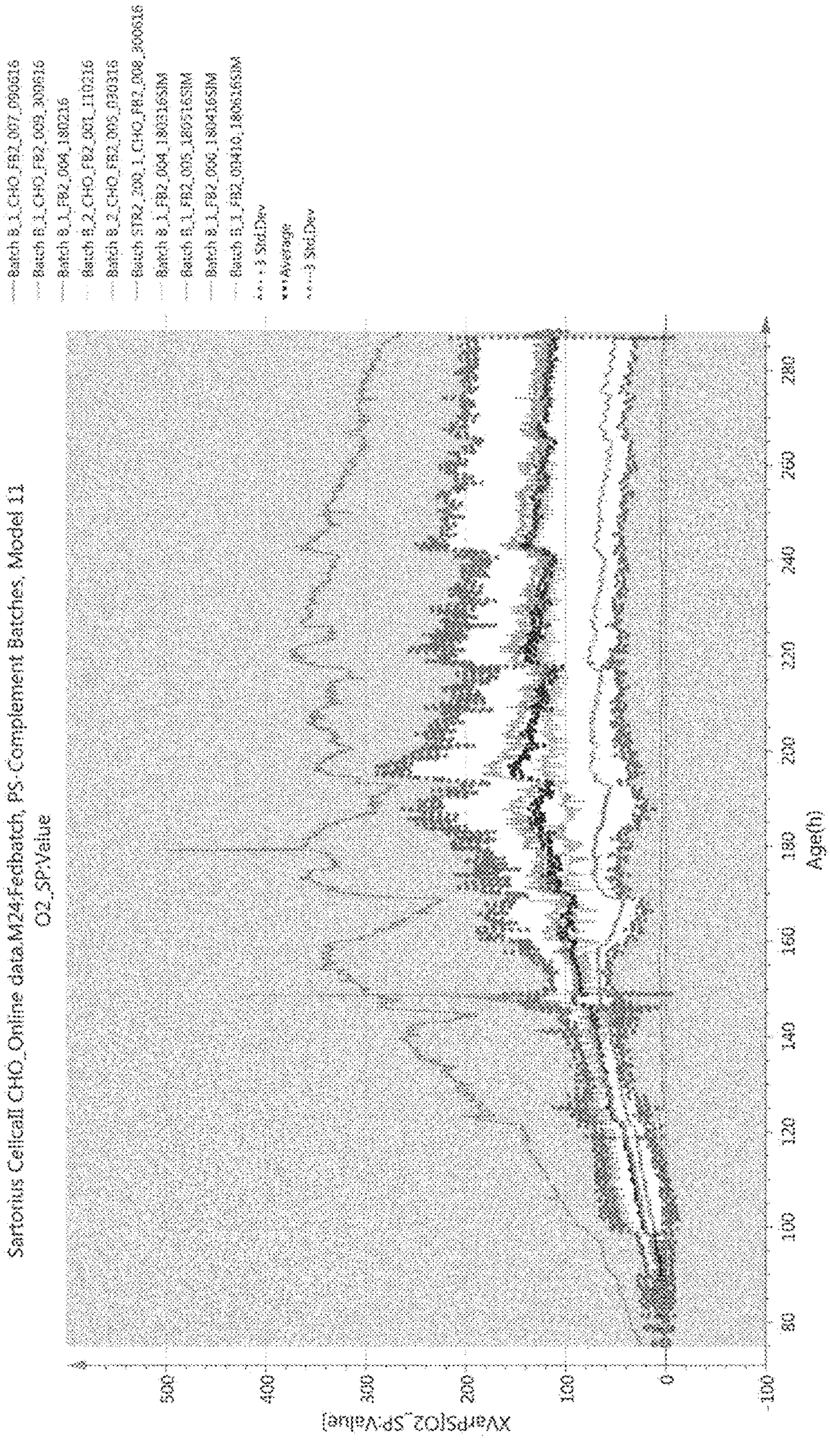
FIG. 11 shows trajectories and a confidence interval for batches of the process including the deviant trajectories.

FIG. 11 shows trajectories of the batches shown in FIG. 10, including deviant trajectories for bad batches. As in FIG. 10, an average of the batch processes and a confidence interval of three standard deviations above and below the average are also plotted.

Figure 12:
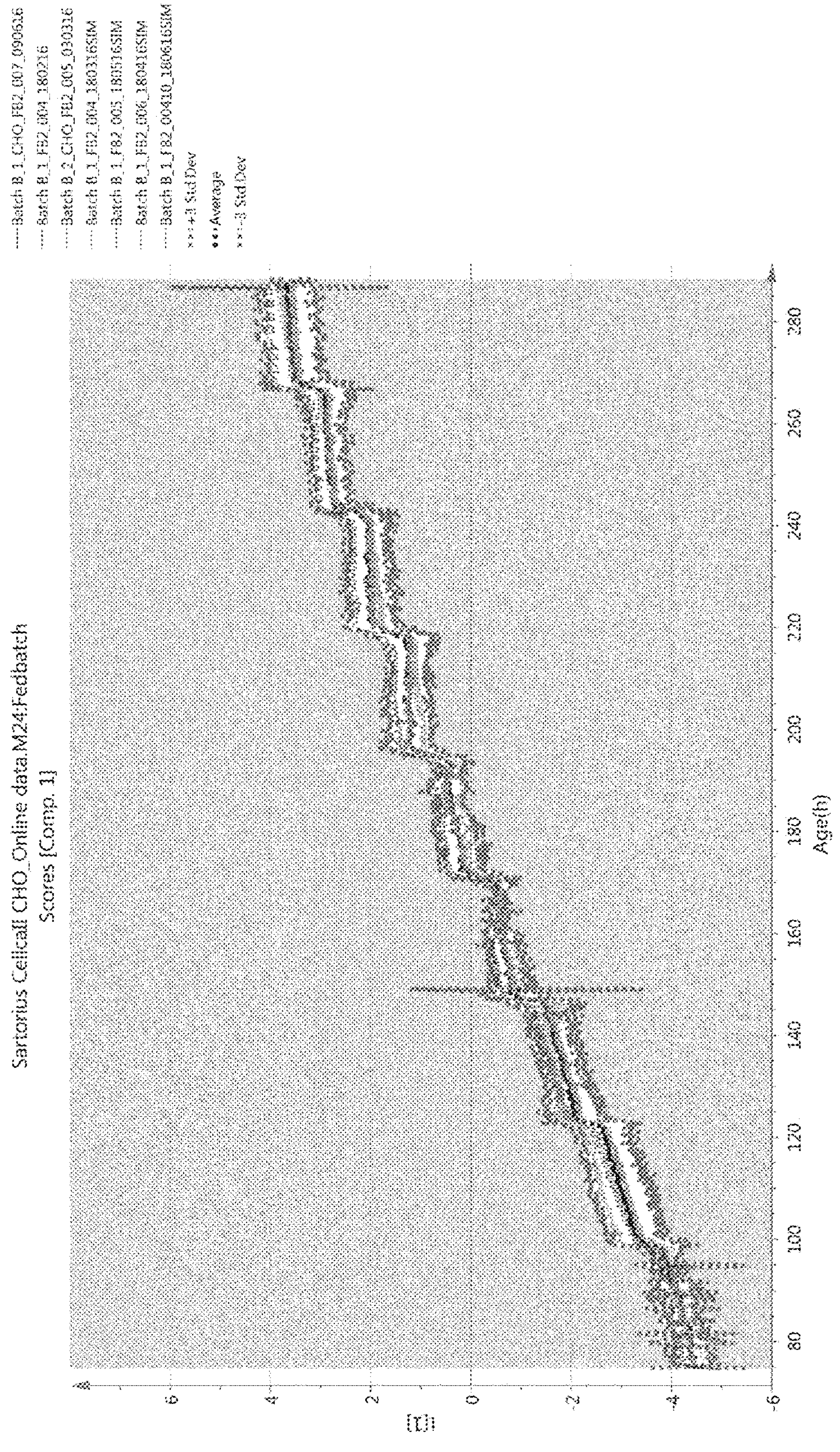
FIG. 12 shows trajectories of batches of a process, a successful trajectory of the process, and a confidence interval of the process.

FIG. 12 shows trajectories of a principal component of batches of a process evaluated over time. In addition, an average for the batches and a confidence interval of three standard deviations above and below the average are also plotted.

Figure 13:
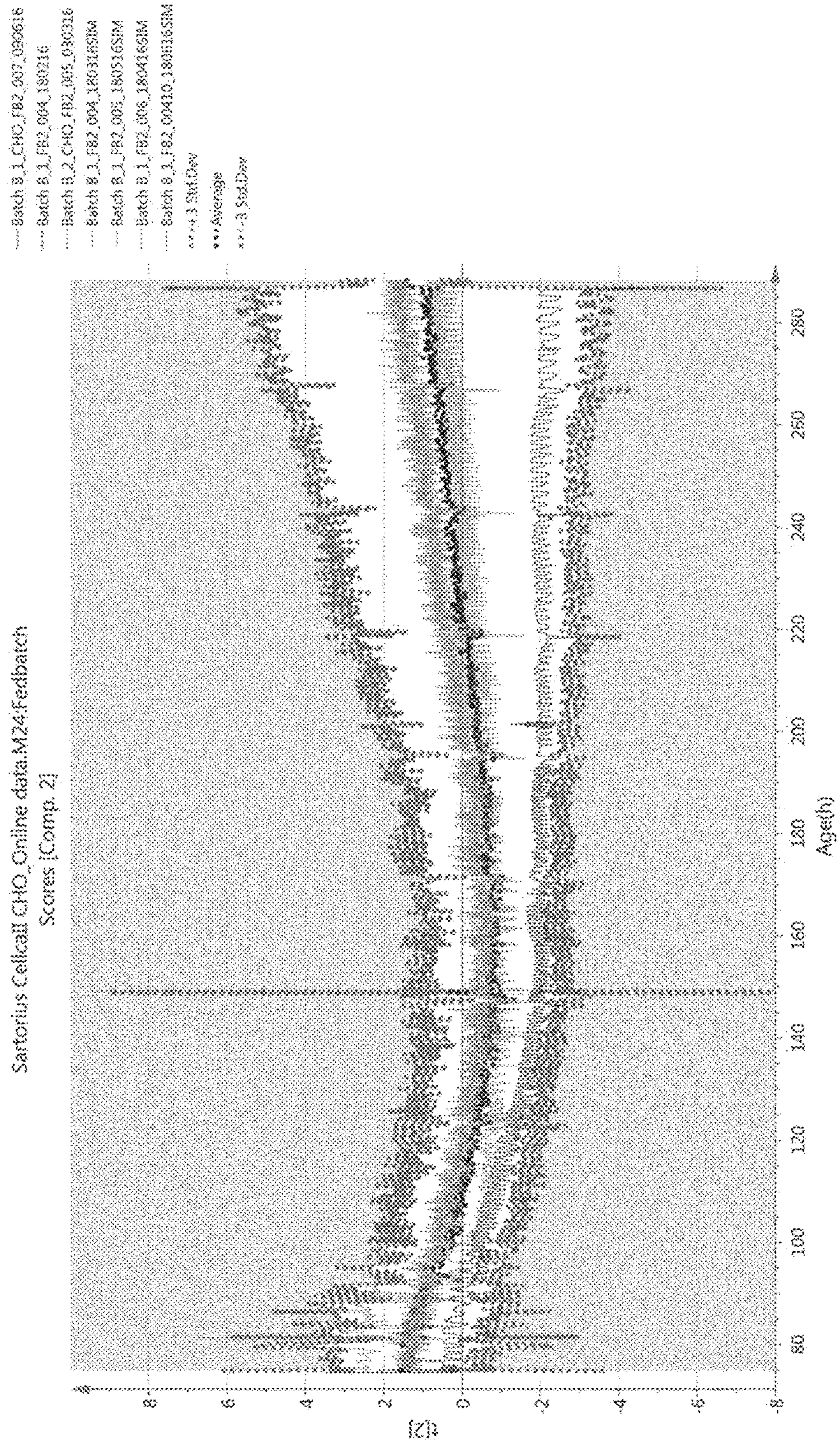
FIG. 13 shows trajectories of batches of the process, a successful trajectory of the process, and a confidence interval of the process.

FIG. 13 shows another chart of a further principal component for the same set of batches shown in FIG. 12. In addition to showing the values of the principal component over time for each batch, the values of an average for all the batches are also plotted along with a confidence interval of three standard deviations above and below the average.

Figure 14:
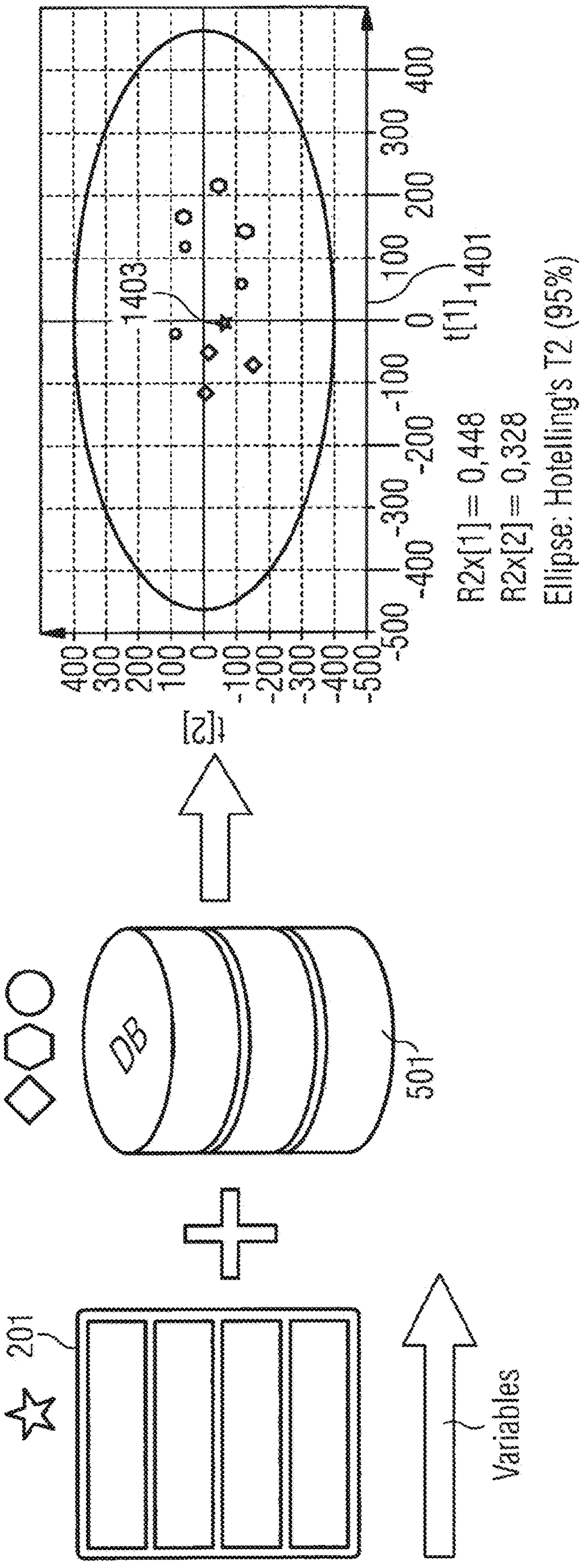
FIG. 14 depicts the identification of a first set of process parameters from the stored sets of process parameters.

FIG. 14 visualizes the identification of the first set of process parameters from the stored sets of process parameters. In particular, the process parameters 201 may be characterizing process parameters provided as initial conditions to the database 501. The process parameters 201 may include a scale or volume of the process, a biological system, and control set points such as pH, and dissolved oxygen. A first set of process parameters may be identified from the stored sets of process parameters based on the characterizing process parameters. In particular, the first set of process parameters may have a specified degree of similarity to the set of characterizing process parameters. The specified degree of similarity may be determined using principal components analysis as described above. In particular, a numerical description of the process may be determined. The numerical description of the process can be visualized in a plot 1401. The numerical description of the process may be derived from the characterizing process parameters and may be visualized as a point 1403 on the plot 1401. Numerical descriptions of a plurality of the stored sets of process parameters are also visualized on the plot 1401.

Figure 15:
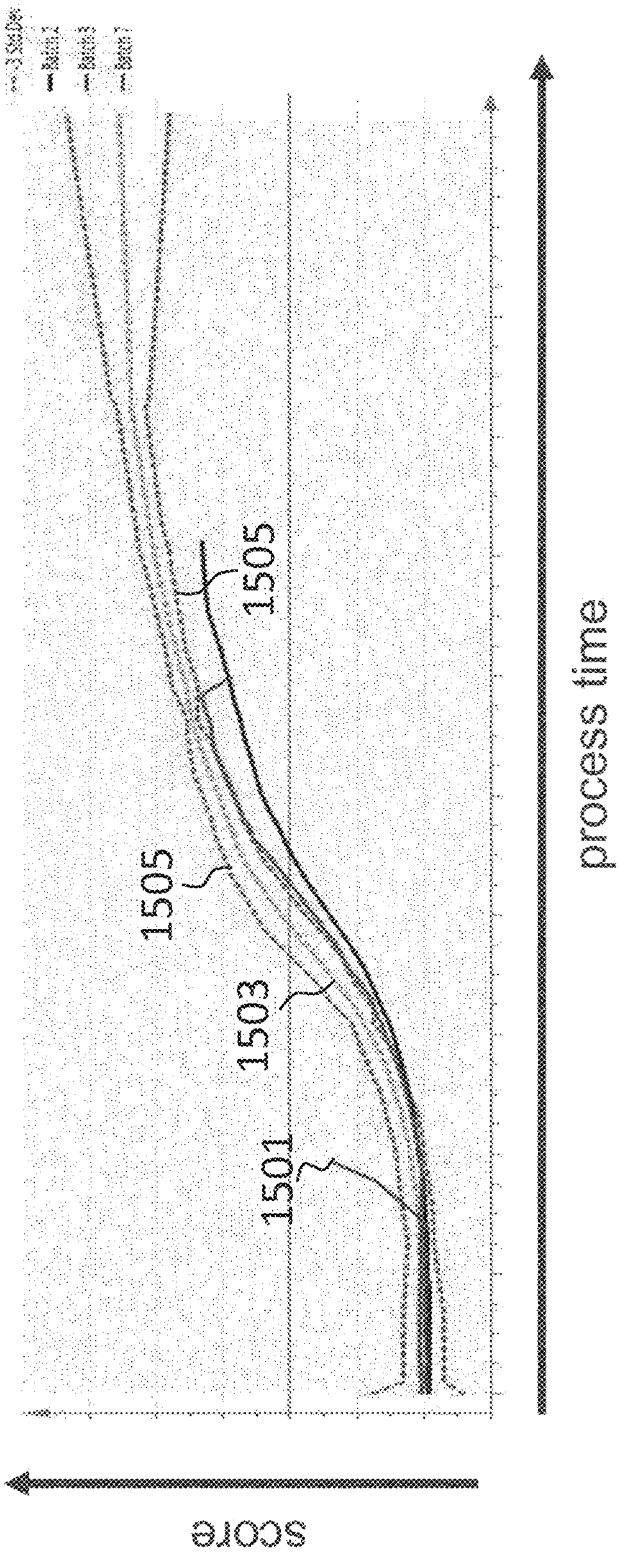
FIG. 15 depicts a successful trajectory, a confidence interval, and failure of a confidence criterion.

FIG. 15 shows when a difference between an estimated trajectory 1501 and a first successful trajectory fails a confidence criterion. In the example of FIG. 15, the estimated trajectory 1501 and the first successful trajectory are plotted as numerical descriptions of process measurements over time. In the context of FIG. 15, the numerical descriptions of process measurements are referred to as scores (i.e. the x-axis is time and the y-axis is the measurement score).

FIG. 15 shows that the estimated trajectory 1501 moves outside a confidence interval 1505. The confidence interval 1505 is defined as three standard deviations higher and lower than the first successful trajectory 1503. The estimated trajectory 1501 is shown moving outside the confidence interval 1505. Therefore, the difference between the estimated trajectory 1501 and the first successful trajectory 1503 fails the confidence criterion. In particular, in the example of FIG. 15, the estimated trajectory is more than three standard deviations above the first successful trajectory 1503. Accordingly, the estimated trajectory 1501 is outside the confidence interval 1505 and therefore fails the confidence criterion.

Figure 16:
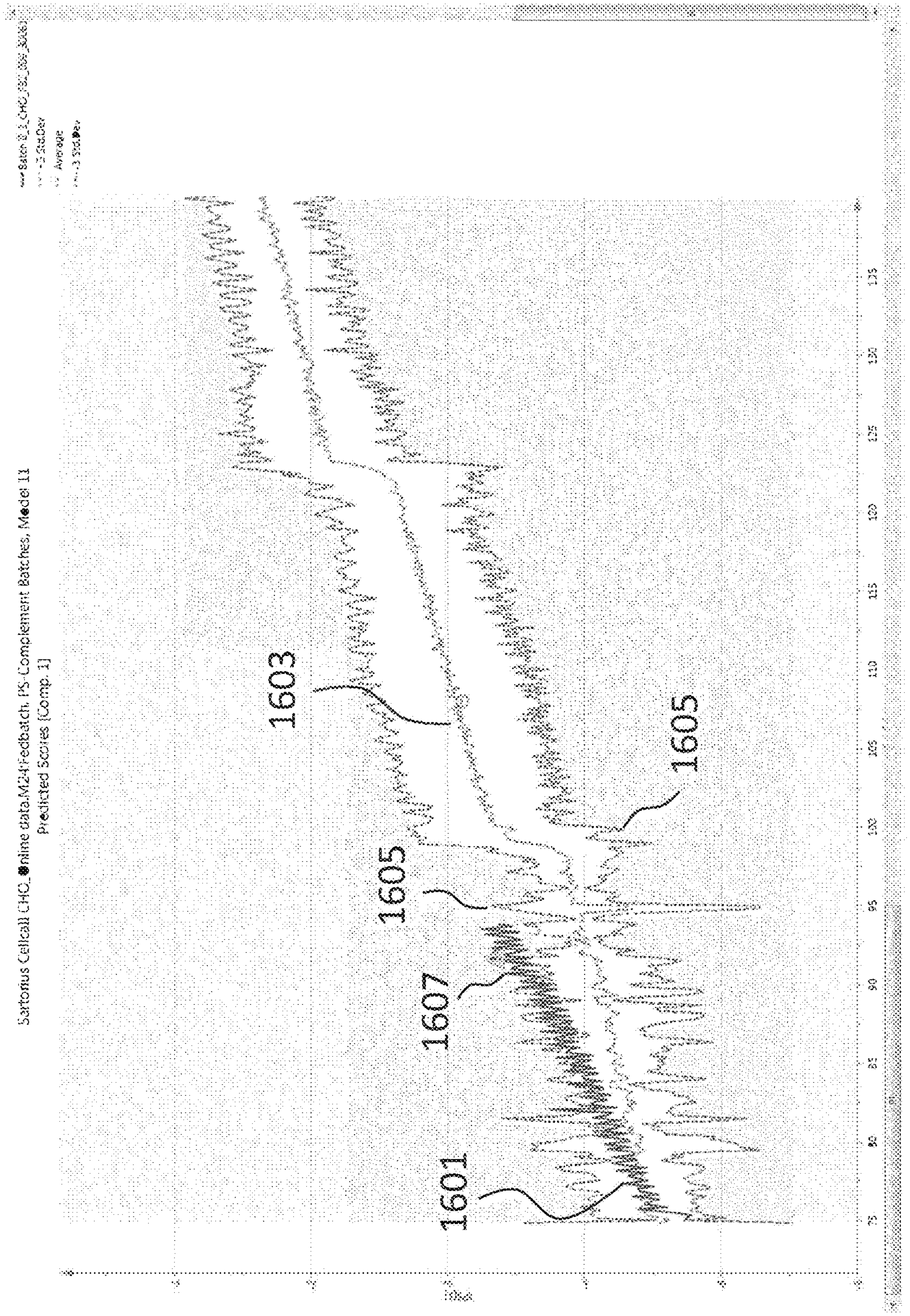
FIG. 16 also depicts a successful trajectory, a confidence interval, failure of a confidence criterion.

FIG. 16 shows another example of when a difference between an estimated trajectory 1601 and a first successful trajectory 1603 fails a confidence criterion. In particular, in the example of FIG. 16, the estimated trajectory 1601 is shown outside a confidence interval 1605 at point 1607 (and at further points on the estimated trajectory 1601) in between hours 90 and 95 as plotted on the x-axis shown in FIG. 16. Accordingly, since the estimated trajectory 1601 is outside the confidence interval 1605 the difference between the estimated trajectory 1601 and the first successful trajectory 1603 fails the confidence criterion.

Figure 17:
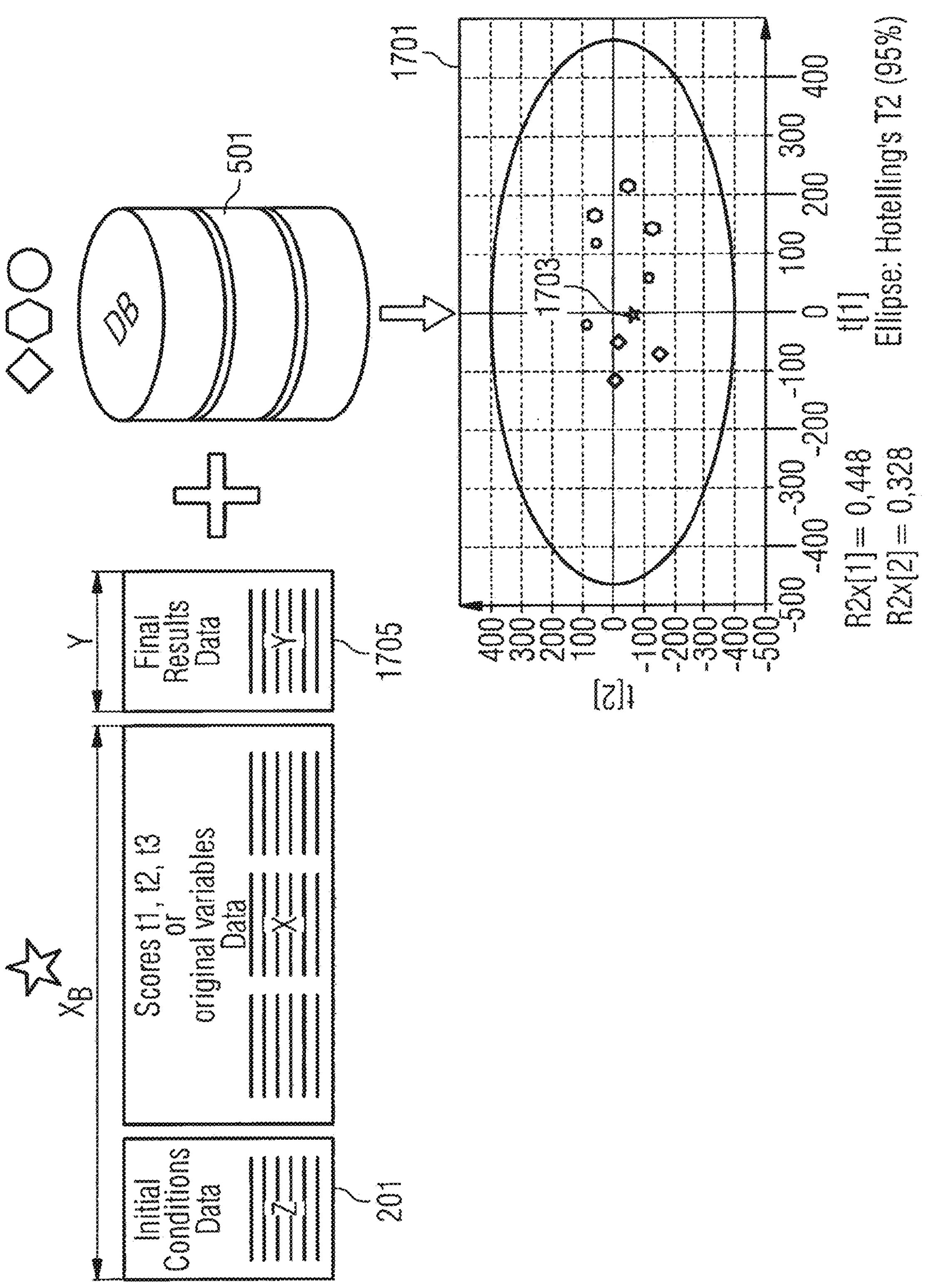
FIG. 17 depicts a similarity comparison to determine one of the stored sets of process parameters.

FIG. 17 shows an example of comparing recorded measurements of the process 203 and the process parameters 201 to a plurality of the stored sets of process parameters stored in the database 501. Accordingly, in addition to the process parameters 201, all further data known about the process 203 may be used to determine a numerical description of the process. This numerical description of the process may be based on recorded measurements of the process possibly including quality attributes depicted in FIG. 17 as final results data 1705. All this data may be used to calculate a numerical description of the process which may be compared with numerical descriptions stored in the database. A plot 1701 showing numerical descriptions includes a numerical description 1703 of the process currently being performed. Although the plot 1701 looks similar to the plot 1401, in general, these plots would appear differently.

Accordingly, as the process is performed its numerical description may evolve such that it is more similar to the numerical description of a different process stored in the database. Then, a second set of process parameters may be determined from the plurality of stored sets of process parameters that has a greater degree of similarity to the set of characterizing process parameters and the recorded measurements than the first set of process parameters.

Figure 18:
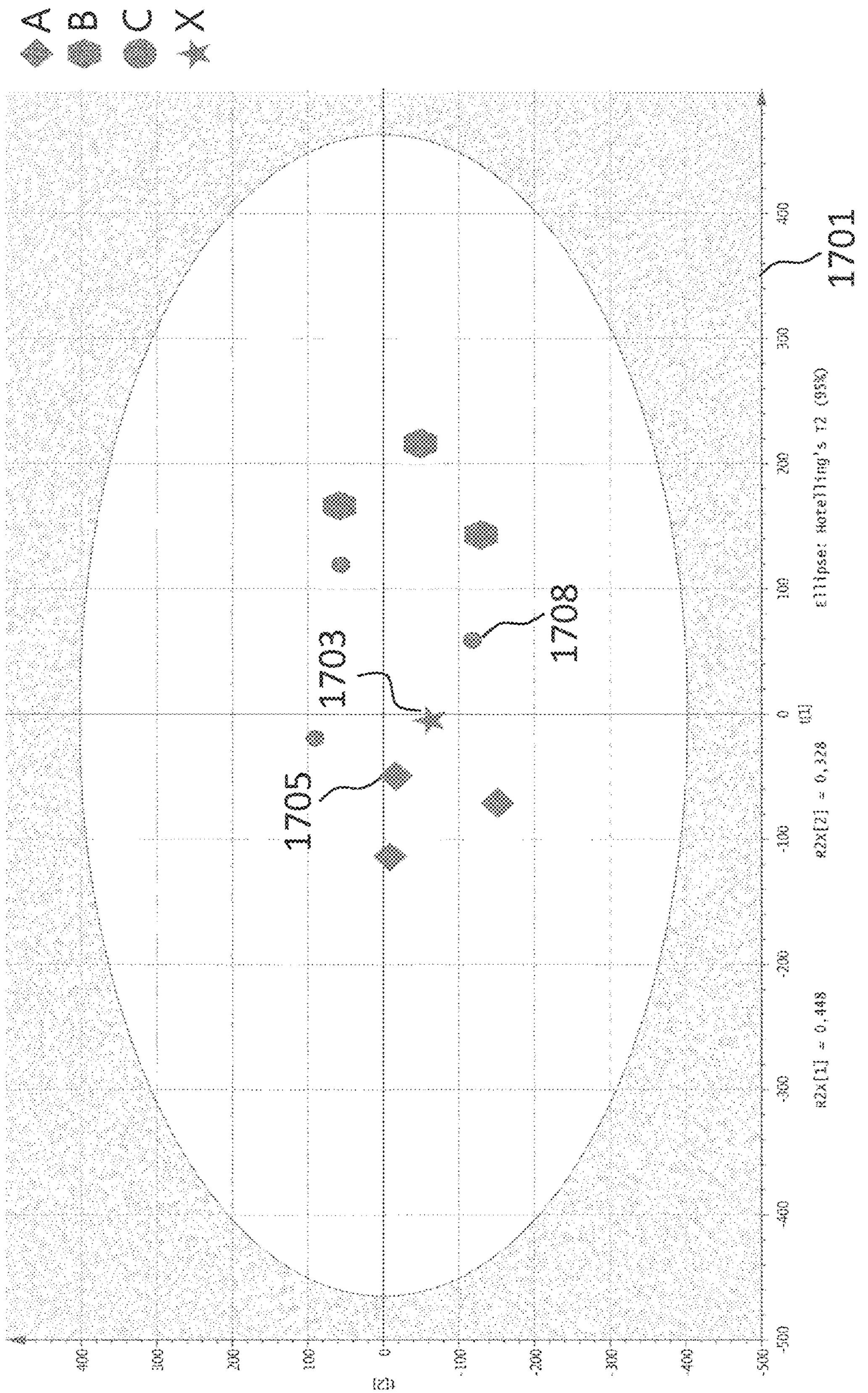
FIG. 18 shows a graph of numerical descriptions processes.

FIG. 18 shows the plot 1701 visualizing numerical descriptions of processes. In particular, the numerical description of the process currently being performed 1703 is shown along with numerical descriptions of processes corresponding to stored sets of process parameters. It can be seen from FIG. 18 that a numerical description of a process 1705 corresponding to a second set of process parameters has a greater degree of similarity to the process currently being performed, depicted as point 1703, than a point 1708, which is a numerical description of a process corresponding to the first set of process parameters. Accordingly, it would be determined that the second set of process parameters, corresponding to the point 1705, has a greater degree of similarity to the set of characterizing process parameters and the recorded measurements, corresponding to the point 1703, than the first set of process parameters.

The invention claimed is:

1. A computer-implemented method comprising:

providing a database, the database storing a plurality of sets of process parameters to control and monitor respective ones of a plurality of processes performed in order to produce biopharmaceutical products, wherein each of the plurality of stored sets of process parameters is associated with a successful trajectory of a respective one of the processes controlled by the respective set of process parameters, wherein each successful trajectory is a time-based profile of measurements recorded during performance of the respective process;

receiving a set of characterizing process parameters that characterize a process for producing a biopharmaceutical product;

querying the database to identify a set of process parameters from the plurality of stored sets of process parameters, the identified set of process parameters having a specified degree of similarity to the set of characterizing process parameters, wherein the identified set of process parameters is associated with an identified successful trajectory, controlling and monitoring the process for producing the biopharmaceutical product using the identified set of process parameters which are associated with the identified successful trajectory, identifying a different set of process parameters and controlling and monitoring the process for producing the biopharmaceutical product using the different set of process parameters, comprising the following steps:

recording measurements of the process for producing the biopharmaceutical product continually during the process to obtain current recorded measurements;

determining a current estimated trajectory of the process for producing the biopharmaceutical product based on the current recorded measurements;

comparing the current estimated trajectory with the identified successful trajectory that is associated with the set of process parameters that is currently being used to control and monitor the process for producing the biopharmaceutical product;

determining that a difference between the current estimated trajectory and the identified successful trajectory that is associated with the set of process parameters that is currently being used to control and monitor the process for producing the biopharmaceutical product fails a predetermined confidence criterion;

querying the database to compare the current recorded measurements and the set of characterizing process parameters to the plurality of the stored sets of process parameters; and selecting, based on the comparison, a set of process parameters from the plurality of stored sets of process parameters that is different from the set of process parameters that is currently being used to control and monitor the process for producing the biopharmaceutical product, and that has a greater degree of similarity to the set of characterizing process parameters and the current recorded measurements than the set of process parameters that is currently being used to control and monitor the process for producing the biopharmaceutical product; and controlling and monitoring the process for producing the biopharmaceutical product using the different set of process parameters; and repeating the steps of identifying the different set of process parameters and controlling and monitoring the process for producing the biopharmaceutical product using the different set of process parameters until it is determined that a finishing condition is met.

2. The method of claim 1, wherein the characterizing process parameters and the stored sets of process parameters include numerical values and text based values;

wherein identifying the set of process parameters comprises identifying a first set of process parameters and identifying the first set of process parameters comprises:

comparing, via multivariate data analysis, numerical values of the set of characterizing process parameters with numerical values of the sets of stored process parameters.

3. The method of claim 1, wherein identifying the set of process parameters comprises identifying a first set of process parameters and identifying the first set of process parameters comprises:

determining, via multivariate analysis, stored process parameters that have an effect on quality attributes included in the characterizing process parameters, wherein the determining may comprise ranking stored process parameters from those having the most significant effect on the included quality attributes to those having the least significant effect on the included quality attributes, wherein the determined process parameters are not included in the characterizing process parameters, wherein the first set of stored process parameters includes the determined process parameters.

4. The method of claim 3, wherein the quality attributes include one or more of the following: misincorporation, glycosylation, recovery, misfolds, aggregation, product concentration, protein concentration, moisture, foreign particles, total mass, drug release rate, and total drug content.

5. The method of claim 3, wherein the quality attributes include one or more of the following: titer, power consumption, a target duration of the process, cell density, and volumetric productivity, wherein volumetric productivity is measured in volume yield of product per unit of time.

6. The method of claim 1, wherein comparing the recorded measurements and the set of characterizing process parameters to the plurality of stored sets of process parameters comprises:

determining a plurality of principal components from the characterizing process parameters and the recorded measurements; and calculating a characterizing numerical description of the process as a function of the plurality of principal components;

wherein identifying the set of process parameters comprises identifying a first set of process parameters and a second set of process parameters, wherein the first set of process parameters includes a first numerical description of the respective process calculated as a function of a plurality of principal components derived from the first set of process parameters;

wherein the second set of process parameters includes a second numerical description of the respective process calculated as a function of a plurality of principal components derived from the second set of process parameters;

wherein determining the second set of process parameters comprises determining that the characterizing numerical description is closer to the second numerical description than the first numerical description; and wherein each principal component may be a linear combination of process parameters.

7. The method of claim 1, wherein the identified successful trajectory includes a first successful trajectory, wherein the first successful trajectory is associated with a standard deviation, wherein the confidence criterion is a function of the standard deviation.

8. The method of claim 1, wherein identifying the set of process parameters comprises identifying a first set of process parameters and the first set of process parameters includes a further process parameter and a corresponding value, wherein the further process parameter is included in the characterizing process parameters, wherein the corresponding value is not included with the characterizing process parameters, wherein controlling and monitoring the process further comprises performing the process using the further process parameter and the corresponding value; and wherein the further process parameter may be a control set point.

9. The method of claim 1, wherein the characterizing process parameters and/or the stored process parameters include at least one of the following:

a description of equipment for performing the process;

a scale of the process;

a type of the process;

a name of the biopharmaceutical product;

a biological system of the process;

quality attributes to measure the quality of the biopharmaceutical product; and a configuration of the equipment.

10. The method of claim 9, wherein the configuration of the equipment includes one or more of the following:

a target duration of the process;

a target temperature;

a stirrer/agitator speed;

a target pH level;

a feed rate;

a target substrate level; and a target dissolved oxygen level.

11. The method of claim 1, wherein the recorded measurements comprise one or more of the following:

a current duration of the process;

a partial pressure of carbon dioxide;

a cell density;

a cell viability;

a substrate concentration;

a metabolite concentration;

a time of infection; and a current temperature.

12. The method of claim 1, wherein the biopharmaceutical product is one of the following: a recombinant protein, a non-recombinant protein, a vaccine, a gene vector, DNA, RNA, an antibiotic, a secondary metabolite, cells for cell therapy or regenerative medicine, an artificial organ.

13. A computer program product comprising non-transitory computer-readable instructions, which, when loaded and executed on a computer system, cause the computer system to perform operations according to the method of claim 1.

14. A computer system operable to control and monitor an industrial process to produce a biopharmaceutical product, the computer system comprising:

a database being configured to:

store sets of process parameters to control and monitor respective ones of a plurality of processes performed in order to produce the biopharmaceutical product, wherein each of the stored sets of process parameters is associated with a successful trajectory of a respective one of the processes controlled by the respective set of process parameters, wherein each successful trajectory is a time based profile of measurements recorded during performance of the respective process; and receive a set of characterizing process parameters that characterize the process;

a processor associated with the database configured to:

identify a first set of process parameters from the stored sets of process parameters, wherein the first set of process parameters has a specified degree of similarity to the set of characterizing process parameters;

a control system, comprising at least one control device, being configured for:

controlling and monitoring the process using the first set of process parameters that is associated with a first successful trajectory, determining a current estimated trajectory of the process based on current recorded measurements, comparing the current estimated trajectory with the successful trajectory that is associated with the set of process parameters that is currently being used to control and monitor the process, and revising, until a finishing condition is met, the set of process parameters that is used to control and monitor the process, and controlling and monitoring the process using a different successful trajectory associated with a different set of process parameters obtained from the revising, wherein revising the set of process parameters comprises:

determining that a difference, between the current estimated trajectory and the successful trajectory that is associated with the set of process parameters that is currently being used to control and monitor the process, fails a predetermined confidence criterion;

querying the database to compare the current recorded measurements and the set of characterizing process parameters to the plurality of the stored sets of process parameters; and obtaining, based on the comparison, a different set of process parameters from the plurality of stored sets of process parameters that has a greater degree of similarity to the set of characterizing process parameters and the current recorded measurements than the identified set of process parameters.

* * * * *